(12) United States Patent
Lübbe

(10) Patent No.: US 9,532,931 B2
(45) Date of Patent: Jan. 3, 2017

(54) POLYSILOXANE COMPOUND AND DENTAL MATERIALS THAT CAN BE PREPARED FROM IT

(71) Applicant: VOCO GmbH, Cuxhaven (DE)

(72) Inventor: Gerrit Lübbe, Cuxhaven (DE)

(73) Assignee: VOCO GMBH, Cuxhaven (DE)

( * ) Notice: Subject to any disclaimer, the term of this patent is extended or adjusted under 35 U.S.C. 154(b) by 0 days.

(21) Appl. No.: 14/728,753

(22) Filed: Jun. 2, 2015

(65) Prior Publication Data

US 2015/0342841 A1 Dec. 3, 2015

(30) Foreign Application Priority Data

Jun. 3, 2014 (DE) ........................ 10 2014 210 432

(51) Int. Cl.
| | |
|---|---|
| *A61K 6/093* | (2006.01) |
| *C07F 7/18* | (2006.01) |
| *A61K 6/00* | (2006.01) |
| *A61K 6/087* | (2006.01) |

(52) U.S. Cl.
CPC ............. *A61K 6/093* (2013.01); *A61K 6/0088* (2013.01); *A61K 6/087* (2013.01); *C07F 7/184* (2013.01); *C07F 7/1816* (2013.01)

(58) Field of Classification Search
None
See application file for complete search history.

(56) References Cited

U.S. PATENT DOCUMENTS

| | | | |
|---|---|---|---|
| 4,243,692 A | 1/1981 | Scholze et al. | |
| 5,063,257 A | 11/1991 | Akahane et al. | |
| 5,717,125 A * | 2/1998 | Wolter ................. | C07F 7/1836 556/413 |
| 5,847,025 A | 12/1998 | Moszner et al. | |
| 6,124,491 A * | 9/2000 | Wolter ................. | C07F 7/1836 204/157.62 |
| 6,566,413 B1 * | 5/2003 | Weinmann ............ | A61K 6/083 424/401 |
| 8,076,441 B2 * | 12/2011 | Wolter ................. | C07F 7/1836 524/588 |
| 8,748,647 B2 * | 6/2014 | Wolter ................. | C07F 7/1836 556/420 |
| 2002/0129736 A1 | 9/2002 | Bui et al. | |
| 2006/0247330 A1 | 11/2006 | Takano et al. | |
| 2007/0142495 A1 | 6/2007 | Neffgen et al. | |
| 2012/0082959 A1 | 4/2012 | Blomker et al. | |
| 2014/0221521 A1 | 8/2014 | Wolter et al. | |
| 2014/0249325 A1 | 9/2014 | Wolter et al. | |
| 2015/0342841 A1 * | 12/2015 | Lubbe ................. | C07F 7/184 523/116 |

FOREIGN PATENT DOCUMENTS

| | | |
|---|---|---|
| CA | 2425953 | 10/2002 |
| EP | 1563821 | 8/2005 |
| JP | H1087671 | 4/1998 |

OTHER PUBLICATIONS

STIC structure search results, 14728753-519960-EICSEARCH, Jul. 21, 2016.*
STIC structure search results, 14728753-519960-EICSEARCH 2, Jul. 26, 2016.*
Watts, D.C., et al., "Determination of polymerization shrinkage kinetics in visible-light materials: methods development," Dental Materials, Oct. 1991, vol. 7, pp. 281-287.

* cited by examiner

*Primary Examiner* — Peter A Salamon
(74) *Attorney, Agent, or Firm* — Duane Morris LLP; J. Rodman Steele, Jr.; Gregory M. Lefkowitz

(57) ABSTRACT

The invention relates to a polysiloxane compound comprising specific siloxane units, curable dental materials comprising one or more than one polysiloxane compound according to the invention, cured dental materials obtainable from the curable dental materials according to the invention, a method for preparation of polysiloxane compounds according to the invention, a method for preparing curable polysiloxane compounds according to the invention and a method for preparing cured dental materials according to the invention.

14 Claims, No Drawings

POLYSILOXANE COMPOUND AND DENTAL MATERIALS THAT CAN BE PREPARED FROM IT

The invention relates to a polysiloxane compound comprising specific siloxane units, curable dental materials comprising one or more than one polysiloxane compound according to the invention, cured dental materials obtainable from the curable dental materials according to the invention, a method for preparing polysiloxane compounds according to the invention, a method for preparing curable polysiloxane compounds according to the invention and a method for preparing cured dental materials according to the invention. Further aspects of the present invention and its preferred configurations are apparent from the following description, the embodiments and claims.

Polysiloxane compounds within the meaning of this text have at least one or more chains, having alternately arranged silicon atoms and oxygen atoms bonded together, wherein organic groups (organic side chains) are bonded to the silicon atoms. These organic groups can differ greatly and as a result lead to a large number of polysiloxane compounds with differing properties. Often these organic groups have one or more organically polymerisable groups (i.e. reactive groups), which for example can react with one or more organically polymerisable groups of another polysiloxane compound and thereby form crosslinked/polymerised polysiloxane compounds.

Polysiloxane compounds have long been known and are obtainable for example by hydrolysis and condensation of silanes having hydrolysable groups (see for example DE 27 58 414 A1) or by hydrosilylation of allyl or vinyl compounds with SiH-containing compounds. Polysiloxane compounds can be further processed to give a multitude of products, for example overlayers, coatings, membranes or bulk materials. This further processing is often based on a crosslinking reaction of organically polymerisable groups in the polysiloxane compounds (e.g. (meth)acrylate groups) and the resulting formation of crosslinked polysiloxane compounds.

A specific group of polysiloxane compounds contains in the organic groups (side chains) apart from an organically polymerisable group, additionally free polar functional groups such as for example hydroxy or carboxy groups.

Thus DE 44 16 857 C1 relates to hydrolysable and polymerisable silanes, to methods for preparation thereof and to the use thereof for preparation of silica(hetero) polycondensates and (hetero)polymerisates. Hydrolysable, organically modified silanes are widely used in the preparation of scratch-resistant coatings for a wide variety of different substrates, for the preparation of fillers, of adhesives and sealing compounds or of moulded articles.

Taking into consideration the teaching of DE 44 16 857 C1, the conceptual approach taken in preparation for our own investigations was that the silica(hetero)polycondensates (polysiloxane compounds) disclosed in DE 44 16 857 C1 can also be used in curable dental materials. It was taken into consideration that these polysiloxane compounds comprise free polar functional groups (e.g. carboxy or hydroxy groups), capable of complexing suitable metal ions/transition metal ions (e.g. ions of titanium, zirconium or tin). In curable dental materials this can have a positive effect on the x-ray opacity, on contact toxicity and on the refractive index of a corresponding curable or cured dental material.

DE 198 60 364 C2 relates to polymerisable dental compositions based on siloxane compounds with the ability to cure, to the use and preparation thereof. In preparation for our own investigations it was taken into consideration that in DE 198 60 364 C2 the preparation of cyclic polysiloxanes and their use as a basis for polymerisable dental compositions is described. Despite a high density of groups capable of polymerisation they should have a low viscosity, allowing a high filler loading, leading to compositions, having low polymerisation shrinkage. Here too, free polar functions are present as well as the polymerisable units in the organic side chains of the polysiloxanes described.

The free polar functional groups, e.g. in the abovementioned polysiloxane compounds, however, regularly lead to undesired properties. Thus our own investigations have shown that the hydrophilicity of the polysiloxane compounds caused by the (free) polar functional groups leads to increased water absorption in the presence of moisture, which reduces the wet strength of the curable dental material in a disadvantageous manner. Presumably due to the formation of internal hydrogen bonds there is an increase in viscosity. This then has an adverse effect on handling in the preparation of the curable dental composition.

There is a considerable need on the part of dental practitioners and the dental industry, to further adapt polysiloxane compounds to the requirements of a modem (curable or cured) dental material and to minimise the abovementioned disadvantages. Such adapted polysiloxane compounds should have improved physical properties for dental purposes (or lead to dentally improved physical properties of the corresponding curable/cured dental materials), e.g. lower polymerisation shrinkage on polymerisation/crosslinking of the polysiloxane compounds (e.g. on curing), increased strength and/or restricted water absorption with simultaneously comfortable consistency of the curable dental material.

Initial success was achieved in improving the polysiloxanes by addition or substitution of various substrates to the free polar functionalities of the abovementioned special polysiloxanes.

EP 1 874 847 B1 relates to a process for the preparation of silanes with two, three or even more structural units which are linked to one another via a urethane-, acid amide- and/or carboxylic acid ester group-containing bridge and each of which contains at least one organically polymerisable radical and at least one silyl radical. These silanes should particularly be suitable for modifying the properties of silica (hetero) polycondensates and silyl group-containing organic polymers (ORMOCER®s). The process disclosed should also be suitable for bridging already pre-condensed silica (hetero) polycondensates.

Taking into consideration the teaching in EP 1 874 847 B1 the conceptual approach taken in preparation for our own investigations was that the silica(hetero)polycondensates (polysiloxane compounds) disclosed in EP 1 874 847 B1 have a free hydroxy group (e.g. a free polar functional group). These free hydroxy groups can react with a dicarboxylic acid derivative or diisocyanate in such a way that hydroxy groups form a bond (bridge) with a dicarboxylic acid derivative or diisocyanate (see the example diagram (a) below). Such linked polysiloxane compounds (compound (101) in example diagram (a)) have a significantly higher molecular weight without any significant reduction in the double bond density (as a result of the organically polymerisable (meth)acrylate groups). Double bond density will be understood by the person skilled in the art to mean the quotient of the number of polymerisable double bonds of a compound and the molecular weight of this compound. The higher molecular weight has a positive effect on the biocompatibility and polymerisation shrinkage on crosslinking of the linked polysiloxane compounds. At the same time it was possible to increase the hydrophobicity of the polysiloxane compounds. From our own investigations, however, it has been found that the higher molecular weight has an adverse effect on the viscosity of the linked polysiloxane compounds (and thus on the processability in the preparation of the curable dental material). The viscosity increases significantly with the degree of linking, e.g. with the molecular weight, so that a tolerable processability in manufacturing a corresponding curable dental material, comprising such linked polysiloxane compounds, is no longer satisfactorily ensured even at a very low degree of linking.

(b) below). The reaction products (see compound (102) in the example Diagram (b)) regularly have increased strength and simultaneously greater hydrophobicity and improved biocompatibility as a result of the increased molecular weight.

Our own investigations have also shown, however, that the introduction of additional polymerisable double bonds in the form of organically polymerisable groups leads to increased polymerisation shrinkage during crosslinking of the polysiloxane compounds, since the double bond density increases significantly, but the rise in molecular weight is only comparatively low.

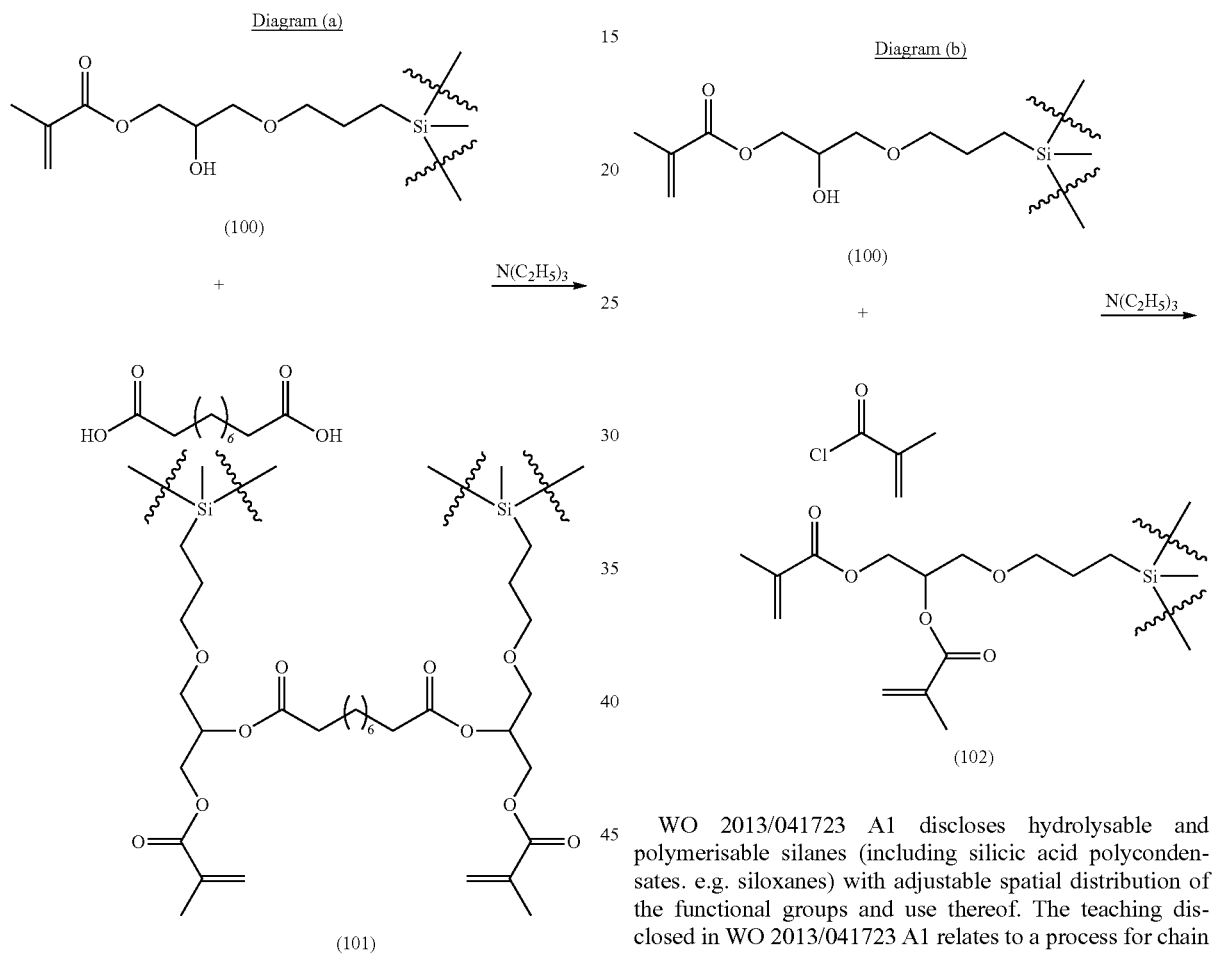

EP 1 685 182 B1 relates to silanes and silicic acid polycondensates and partial condensates formed therefrom, in which an organic radical bonded to a silicon is present, which is branched and bears at least one independently organically polymerisable group at each of the two branches or bears such a group at one of the branches and has a radical having a further silicon atom at the other.

The polysiloxanes disclosed in EP 1 685 182 B1 also comprise free polar functional groups in the form of hydroxy groups. Taking into consideration the teaching in EP 1 685 182 B1 the conceptual approach taken in preparation for our own investigations was that by reaction carboxylic acid or isocyanate derivatives, which for their part similarly comprise polymerisable double bonds in the form of organically polymerisable groups (e.g. (meth)acrylate groups), can be linked to free polar functional groups (see example Diagram WO 2013/041723 A1 discloses hydrolysable and polymerisable silanes (including silicic acid polycondensates. e.g. siloxanes) with adjustable spatial distribution of the functional groups and use thereof. The teaching disclosed in WO 2013/041723 A1 relates to a process for chain extension of radicals bonded to silicon via carbon in silanes or siloxanes.

WO 2013/053693 A1 discloses silicic acid polycondensates (siloxanes) having cyclic olefin-containing structures and methods for the production thereof. WO 2013/053693 A1 discloses that polymer materials having moduli of elasticity that can be adjusted over broad ranges with high elastic expansion (e.g. without brittleness) and thus a high fracture toughness which can be prepared from silicic acid (hetero) polycondensates with cyclic olefin-containing structures.

The problem for the invention was to provide a polysiloxane compound which does not have, or at least only to a lesser extent, the abovementioned disadvantages. The polysiloxane compound to be provided should preferably result in one, more or in particular all the properties mentioned below, in particular when used in a curable or cured dental material (and in particular in comparison with polysiloxane compounds of the type shown as a starting material in diagrams (a) and (b) and a polysiloxane compound bearing a free polar functional group):

good viscosity of the polysiloxane compounds (the viscosity should be 50 Pa·s or less at a temperature of 25° C.) and an associated exceptional processability in the preparation of a curable dental material containing the polysiloxane compounds,
good hydrophobicity
good strength, in particular good flexural strength,
very low polymerisation shrinkage during crosslinking of the polysiloxane compounds, e.g. during curing of the curable dental material,
good biocompatibility,
a refractive index which is almost identical to the refractive index of conventional dental glass (preferably even almost identical to the refractive index of particularly radiopaque barium or zirconium glasses).

The problem indicated above is solved according to the invention by a polysiloxane compound comprising (A) one, two, three or more than three in each case structurally identical first siloxane units selected from the group consisting of siloxane units of the general formula (I)

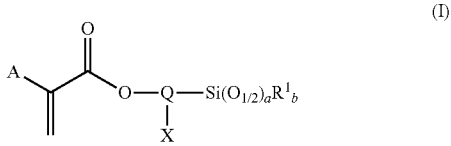

(I)

wherein for the structural units A, Q, X and $R^1$ in each of the structurally identical first siloxane units independently of one another the following applies:
A denotes H or $CH_3$,
Q denotes a link group bearing substituent X.
$R^1$ denotes an alkyl radical with a total of 1 to 4 carbon atoms and
X is selected from the group consisting of
  branched, saturated, unsubstituted alkyl radical with a total of 7 to 18 carbon atoms.
  unbranched, saturated, unsubstituted alkyl radical with a total of 7 to 18 carbon atoms.
  unsubstituted or alkyl substituted aryl radical with a total of 10 to 18 carbon atoms, wherein the alkyl substituent in the alkyl substituted aryl radical is branched and saturated
    or
  unbranched and saturated
  and
  Z—(CO)—$R^2$, wherein herein for the structural units Z and $R^2$ independently of one another and independently of what the structural units A, Q and $R^1$ denote the following applies:
  Z denotes O, S or NH, preferably O
  and
  $R^2$ is selected from the group consisting of
    branched, saturated, unsubstituted alkyl radical with a total of 6 to 18 carbon atoms,
    unbranched, saturated, unsubstituted alkyl radical with a total of 6 to 18 carbon atoms,
    unsubstituted or alkyl substituted aryl radical with a total of 9 to 18 carbon atoms, wherein the alkyl substituent in the alkyl substituted aryl radical is
      branched and saturated
      or
      unbranched and saturated,
    wherein
    b denotes 0, 1 or 2 and
    a denotes 3-b.

The polysiloxane compound according to the invention is a dimer, oligomer or polymer, comprising a first siloxane unit of general formula (I) or two, three or more than three in each case structurally identical first siloxane units of general formula (I). In the above structural formula (and in all corresponding formulas that follow) $O_{1/2}$ denotes the oxygen link to the next silicon atom in a polysiloxane compound according to the invention.

$R^1$ denotes preferably methyl, ethyl, n-propyl, iso-propyl, n-butyl, iso-butyl, sec-Butyl or tert-Butyl.

In the polysiloxane compound according to the invention an "alkyl radical" (where there is a sufficient number of carbon atoms) can be a cycloalkyl radical or comprise a cycloalkyl radical. That is to say that an "alkyl radical" of a polysiloxane compound according to the invention
  comprises or does not comprise a cycloalkyl radical,
  or
  is or is not a cycloalkyl radical.

In other words, a carbon atom of the alkyl radical (as defined above) can be linked with another carbon atom of this alkyl radical with the formation of a ring.

The one first siloxane unit or the several in each case structurally identical first siloxane units of general formula (I) in each case have an organically polymerisable group in the form of a (meth)acrylate group (A denotes H or $CH_3$). The double bonds of these (meth)acrylate groups allow crosslinking/polymerisation with corresponding further organically polymerisable groups (or their double bonds). Preferably the double bond density in the polysiloxane compound according to the invention is exclusively determined by the (meth)acrylate groups in the respective siloxane units of general formula (I). This means that the substituent X (as defined above) preferably contains no additional organically polymerisable double bonds (in the form of organically polymerisable groups) (as for example they would be contained in additional (meth)acrylate groups). Rather the substituents X are preferably selected such that they contain no organically polymerisable double bonds, but significantly increase the molecular weight of the polysiloxane compound according to the invention while simultaneously raising the hydrophobicity. The properties sought are (better) achieved in this way.

The double bond density in the polysiloxane compounds according to the invention, due to the presence of the substituents X, is comparatively low (e.g. compared with a polysiloxane compound not according to the invention, the siloxane units of which instead of the substituent X in each case comprise a hydroxy group, see simply as an example the compound (100) not according to the invention in the example Diagram (a)). Due to the presence of the substituents X the polysiloxane compound according to the invention has a comparatively higher molecular weight.

It could therefore be expected that the comparatively reduced double bond density would lead to a comparatively poorer crosslinking/polymerisation (e.g. compared with a polysiloxane compound not according to the invention, the siloxane units of which instead of the substituent X in each case comprise a hydroxy group, see simply as an example compound (100) in the example diagram (a)) and thus to a comparatively low strength of a corresponding cured dental material. It could also be expected that the comparatively higher molecular weight due to the presence of the substituent X would have adverse effects on the material properties such as for example the viscosity of the polysiloxane compound according to the invention (e.g. a comparative increase in the viscosity) (again for example compared with a polysiloxane compound not according to the invention, the siloxane units of which instead of the substituent X in each case comprise a hydroxy group, see again simply as an example compound (100) in the example Diagram (a)) with good processability in the preparation of a corresponding curable dental material thus no longer being guaranteed.

Contrary to these expectations our own investigations surprisingly showed that the strength, in particular the flexural strength of the corresponding cured dental material (and thus the crosslinking/polymerisation of the polysiloxane compound according to the invention) remains at a very good level and in many cases even increases, the viscosity of the polysiloxane compound according to the invention in comparison is not adversely changed (that is to say in any case not substantially increased) and thus its processability in the preparation of the corresponding curable dental materials is guaranteed even further.

The surprising results cannot yet be fully explained. Our own investigations, however, lead to a number of assumptions and explanatory approaches:

It can be assumed that the substituents X defined above lead to an intramolecular spatial expansion within the polysiloxane compound according to the invention. In turn this could have the effect of increasing the accessibility/reactivity of the organically polymerisable double bonds in the (meth)acrylate groups, so that a larger number of these (meth)acrylate groups are available for a crosslinking/polymerisation reaction with other organically polymerisable double bonds. This could explain why despite a comparatively lower double bond density the strength, in particular the flexural strength of the corresponding cured dental material remains at a very good level and in many cases is even increased.

It can furthermore be assumed that the viscosity of the polysiloxane compound according to the invention is therefore in any case only insignificantly increased (compared to a polysiloxane compound not according to the invention, the siloxane units of which instead of the substituent X in each case comprise a hydroxy group, see again simply as an example compound (100) in the example Diagram (a)), because a free polar hydroxy group due to intermolecular polar interactions (e.g. in the form of hydrogen bonds), in addition to the molecular weight makes a considerable contribution to the viscosity of this polysiloxane compound. A polysiloxane compound according to the invention, comprising one first or two, three or more than three identical first siloxane units of general formula (I), has in these siloxane units no free polar hydroxy group, so that the contribution to the viscosity by intermolecular polar interactions is probably eliminated. The contribution to the viscosity by the increased molecular weight is thus probably to some extent compensated by the elimination of intermolecular polar interactions (or their contribution to the viscosity), so that in any case there remains a lower contribution to the viscosity by the increased molecular weight.

It is also currently assumed that the assumptions made above in relation to X at least to some extent also apply if X is equal to Z—(CO)—$R^2$ (in particular if Z is oxygen). That stated above applies to $R^2$ by analogy.

Polysiloxane compounds according to the invention have a refractive index. Our own investigations in this regard have shown that the refractive index level of the polysiloxane compounds according to the invention is particularly high if X or $R^2$ is an aryl radical (as defined above, preferably an aryl radical designated as preferred above or below). Such polysiloxane compounds according to the invention are particularly preferred. These preferred polysiloxane compounds according to the invention preferably have a refractive index ranging from 1.48 to 1.54. It was particularly surprising that (apart from this preferred refractive index range) the good viscosity of the polysiloxane compound according to the invention is simultaneously maintained and additionally the strength, in particular the flexural strength of a corresponding cured dental material remains at a very good level.

The provision of suitable polysiloxane compounds with specific refractive indices is generally very important for dental applications. Curable dental materials regularly comprise one or more crosslinkable compounds together with fillers, in particular fillers in the form of dental glasses. Such dental glasses have a refractive index. If the refractive index of the dental glasses deviates significantly from the refractive index of the crosslinkable compound(s), during light curing the curable dental material is not penetrated sufficiently by the light due to insufficient translucence (further statements on curing can be found further on in the text). If on the other hand the refractive index of the dental glasses and the refractive index of the crosslinkable compound(s) are within a narrow range, the translucence of the curable dental material increases, allowing exceptional light curing to take place. The invention provides polysiloxane compounds according to the invention having a refractive index suitable for dental glass. The invention allows dental glasses with a high refractive index which previously it was not advisable to use in curable dental materials, to be used as a filler; for only now are polysiloxane compounds according to the invention with a correspondingly high refractive index available. This is true in particular of radiopaque barium and/or zirconium glasses.

Our own investigations have further shown that a polysiloxane compound according to the invention, for which the following applies: X or $R^2$ is an aryl radical as described above (preferably an aryl radical defined as preferred above or below), in a corresponding cured dental material (as defined below) regularly leads to an increased flexural strength and an increased modulus of elasticity, compared with a polysiloxane compound not according to the invention comprising a free polar functional group (see again and simply as an example compound (100) according to example Diagram (a) or (b)).

In addition, our own investigations have shown that the viscosity of a polysiloxane compound according to the invention or a corresponding curable dental material is comparatively low if X or $R^2$ is an alkyl radical defined above (preferably an alkyl radical designated as preferred above or below) (compared with a polysiloxane compound according to the invention, in which X or $R^2$ is an aryl radical). In this case (reduced viscosity) the flow behaviour of this polysiloxane compound according to the invention or of such a curable dental material is correspondingly comparatively high.

Our own investigations have similarly shown that polysiloxane compounds according to the invention in comparison with polysiloxane compounds not according to the invention, bearing a free polar functional group (see again simply as an example compound (100) according to example Diagram (a) or (b)) when applied in a cured dental material regularly lead to reduced polymerisation shrinkage on curing of the corresponding curable dental material.

Preference is for a polysiloxane compound according to the invention (as described above), further comprising
(B) one, two, three or more than three, in each case structurally identical second siloxane units, which are structurally different from the first siloxane unit.

Particular preference is for a polysiloxane compound according to the invention (as defined above, preferably as defined above as preferred), wherein the following applies:
X is selected from the group consisting of
  branched, saturated, unsubstituted alkyl radical with a total of 11 to 18, preferably 11 to 14 carbon atoms.
  unbranched, saturated, unsubstituted alkyl radical with a total of 11 to 18, preferably 11 to 14 carbon atoms,
  unsubstituted or alkyl substituted aryl radical with a total of 11 to 18, preferably 11 to 14 carbon atoms, wherein the alkyl substituent in the alkyl substituted aryl radical is
  branched and saturated
  or
  unbranched and saturated
  and
  Z—(CO)—R², wherein herein for the structural units Z and R² independently of one another and independently of what the structural units A, Q and R¹ denote the following applies:
  Z denotes O, S or NH, preferably O
  and
  R² is selected from the group consisting of
    branched, saturated, unsubstituted alkyl radical with a total of 10 to 18, preferably 10 to 14 carbon atoms,
    unbranched, saturated, unsubstituted alkyl radical with a total of 10 to 18, preferably 10 to 14 carbon atoms,
    unsubstituted or alkyl substituted aryl radical with a total of 10 to 18, preferably 10 to 14 carbon atoms, wherein the alkyl substituent in the alkyl substituted aryl radical
    branched and saturated
    or
    unbranched and saturated.

A polysiloxane compound according to the invention can have a multitude of chemical structures and in particular configurations and constitutions. Preference is for a polysiloxane compound according to the invention (as defined above, preferably as defined above as preferred), wherein the polysiloxane compound is selected from the group consisting of linear polysiloxane, branched polysiloxane, monocyclic polysiloxane, polycyclic polysiloxane, chemically crosslinked polysiloxane and mixed types thereof, wherein the polycyclic polysiloxane is a clathrate compound or is not a clathrate compound.

Particular preference is for a polysiloxane compound according to the invention selected from the group consisting of linear polysiloxane and monocyclic polysiloxane.

For many applications preference is for a polysiloxane compound according to the invention (as defined above, preferably as defined above as preferred), comprising as structural unit (B) or as a further structural unit
one, two, three or more than three structurally identical siloxane units, which are structurally different from the first siloxane unit, but are similarly selected from the group consisting of siloxane units of general formula (I) as defined above or below (preferably as defined above or below as preferred)
or
one, two, three or more than three structurally identical siloxane units, which are structurally different from the first siloxane unit and which are not selected from the group consisting of siloxane units of general formula (I) as defined above or below (preferably as defined above or below as preferred).

Preference is for a polysiloxane compound according to the invention (as defined above, preferably as defined above as preferred), wherein
the link group Q bearing the substituent X comprises a carbon chain linking the oxygen atom bonded to Q with the silicon atom bonded to Q, wherein
the carbon chain is uninterrupted or interrupted by one, two or more than two heteroatoms, wherein
the one, two or more than two heteroatoms independently of one another are selected from the group consisting of O, S and N, preferably O
and/or
the substituent X is directly bonded to a carbon atom of the shortest chain, linking the oxygen atom bonded to Q with the silicon atom bonded to Q.

The invention also relates to a polysiloxane compound (preferably as defined above, particularly preferably as defined above as preferred), comprising
(A) one, two, three or more than three in each case structurally identical first siloxane units selected from the group consisting of siloxane units of the general formula (Ia)

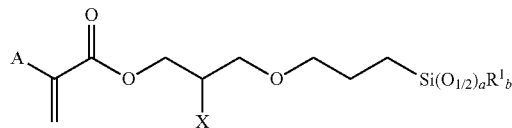

(Ia)

wherein for the structural units A, X and R¹ in each of the structurally identical first siloxane units independently of one another the following applies:
A denotes H or CH₃,
R¹ denotes an alkyl radical with a total of 1 to 4 carbon atoms
and
X is selected from the group consisting of
  branched, saturated, unsubstituted alkyl radical with a total of 7 to 18 carbon atoms, preferably 11 to 18 carbon atoms, particularly preferably 11 to 14 carbon atoms,
  unbranched, saturated, unsubstituted alkyl radical with a total of 7 to 18 carbon atoms, preferably 11 to 18 carbon atoms, particularly preferably 11 to 14 carbon atoms,
  unsubstituted or alkyl substituted aryl radical with a total of 10 to 18 carbon atoms, preferably 11 to 18 carbon atoms, particularly preferably 11 to 14 carbon atoms, wherein the alkyl substituent in the alkyl substituted aryl radical is
  branched and saturated
  or
  unbranched and saturated
  and
  Z—(CO)—R², wherein herein for the structural units Z and R² independently of one another and independently of the meaning of the structural units A and $R^1$ the following applies:
Z denotes O, S or NH, preferably O
and
$R^2$ is selected from the group consisting of
  branched, saturated, unsubstituted alkyl radical with a total of 6 to 18 carbon atoms, preferably 10 to 18 carbon atoms, particularly preferably 10 to 14 carbon atoms,
  unbranched, saturated, unsubstituted alkyl radical with a total of 6 to 18 carbon atoms, preferably 10 to 18 carbon atoms, particularly preferably 10 to 14 carbon atoms,
  unsubstituted or alkyl substituted aryl radical with a total of 9 to 18 carbon atoms, preferably 10 to 18 carbon atoms, particularly preferably 10 to 14 carbon atoms, wherein the alkyl substituent in the alkyl substituted aryl radical is
    branched and saturated
  or
    unbranched and saturated,
  wherein
    b denotes 0, 1 or 2 and
    a denotes 3-b
and
(B) one, two, three or more than three, in each case structurally identical second siloxane units, which are structurally different from the first siloxane unit.

The invention further relates to a polysiloxane compound (preferably as defined above, particularly preferably as defined above as preferred), comprising
(A) one, two, three or more than three in each case structurally identical first siloxane units selected from the group consisting of siloxane units of the general formula (Ib)

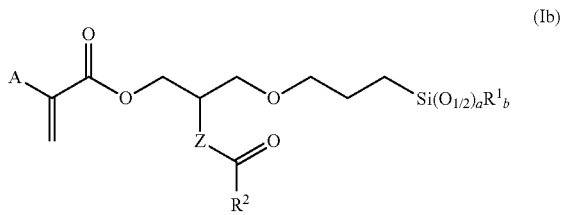

(Ib)

wherein for the structural units A, Z, $R^1$ and $R^2$ in each of the structurally identical first siloxane units independently of one another the following applies:
A denotes H or $CH_3$,
$R^1$ denotes an alkyl radical with a total of 1 to 4 carbon atoms,
Z denotes O, S or NH, preferably O
and
$R^2$ is selected from the group consisting of
  branched, saturated, unsubstituted alkyl radical with a total of 6 to 18 carbon atoms, preferably 10 to 18 carbon atoms, particularly preferably 10 to 14 carbon atoms,
  unbranched, saturated, unsubstituted alkyl radical with a total of 6 to 18 carbon atoms, preferably 10 to 18 carbon atoms, particularly preferably 10 to 14 carbon atoms,
  unsubstituted or alkyl substituted aryl radical with a total of 9 to 18 carbon atoms, preferably 10 to 18 carbon atoms, particularly preferably 10 to 14 carbon atoms, wherein the alkyl substituent in the alkyl substituted aryl radical is
    branched and saturated
  or
    unbranched and saturated,
  wherein
    b denotes 0, 1 or 2 and
    a denotes 3-b
and
(B) one, two, three or more than three, in each case structurally identical second siloxane units, which are structurally different from the first siloxane unit.

Particular preference is for a polysiloxane compound according to the invention (as defined above, preferably as defined above as preferred), comprising
(A) one, two, three or more than three in each case structurally identical first siloxane units selected from the group consisting of siloxane units of the general formula (Ic)

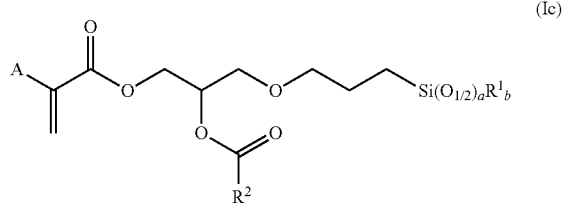

(Ic)

wherein for the structural units A, $R^1$ and $R^2$ in each of the structurally identical first siloxane units independently of one another the following applies:
A denotes H or $CH_3$,
$R^1$ denotes an alkyl radical with a total of 1 to 4 carbon atoms,
and
$R^2$ is selected from the group consisting of
  branched, saturated, unsubstituted alkyl radical with a total of 6 to 18 carbon atoms, preferably 10 to 18 carbon atoms, particularly preferably 10 to 14 carbon atoms,
  unbranched, saturated, unsubstituted alkyl radical with a total of 6 to 18 carbon atoms, preferably 10 to 18 carbon atoms, particularly preferably 10 to 14 carbon atoms,
  unsubstituted or alkyl substituted aryl radical with a total of 9 to 18 carbon atoms, preferably 10 to 18 carbon atoms, particularly preferably 10 to 14 carbon atoms, wherein the alkyl substituent in the alkyl-substituted aryl radical is
    branched and saturated
  or
    unbranched and saturated,
  wherein
    b denotes 0, 1 or 2 and
    a denotes 3-b
and
(B) one, two, three or more than three, in each case structurally identical second siloxane units, which are structurally different from the first siloxane unit.

Quite particular preference is for a polysiloxane compound according to the invention (as defined above, preferably as defined above as preferred), wherein $R^2$ is selected from the group consisting of

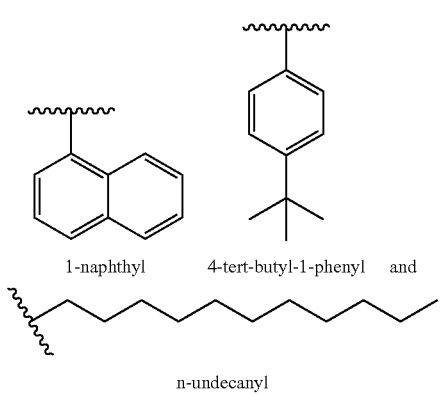

1-naphthyl    4-tert-butyl-1-phenyl    and n-undecanyl

The serpentine lines shown in the structural formulas given above in each case identify the $R^2$ with the adjacent carbon atom of group Z—(CO)—$R^2$ of the chemical bond linking the polysiloxane compound according to the invention.

The term n-undecanyl denotes an alkyl radical (derived from the alkane n-undecane) with formula $CH_3(CH_2)_gCH_2$—, wherein the dash in the formula denotes the linking chemical bond. In the present text the term n-undecanyl is synonymous with the term n-undecyl.

In particular, preference is for a polysiloxane compound according to the invention (as defined above, preferably as defined above as preferred), comprising (A) one, two, three or more than three in each case structurally identical first siloxane units selected from the group consisting of:

| No. | Siloxane unit | A | $R^1$ | $R^2$ |
|---|---|---|---|---|
| (1) | [structure with $Si(O_{1/2})_a(CH_3)_b$] | $CH_3$ | $CH_3$ | 1-naphtyl |
| (2) | [structure with $Si(O_{1/2})_a(CH_3)_b$] | $CH_3$ | $CH_3$ | 4-tert.-butyl-1-phenyl |
| (3) | [structure with $Si(O_{1/2})_a(CH_3)_b$] | $CH_3$ | $CH_3$ | n-undecanyl |

| No. | Siloxane unit | A | R¹ | R² |
|---|---|---|---|---|
| (4) | (acrylate-glyceryl-naphthoate-propoxy-siloxane structure) $Si(O_{1/2})_a(CH_3)_b$ | H | $CH_3$ | 1-naphtyl |
| (5) | (acrylate-glyceryl-4-tert-butylbenzoate-propoxy-siloxane structure) $Si(O_{1/2})_a(CH_3)_b$ | H | $CH_3$ | 4-tert.-butyl-1-phenyl |
| (6) | (acrylate-glyceryl-laurate-propoxy-siloxane structure) $Si(O_{1/2})_a(CH_3)_b$ | H | $CH_3$ | n-undecanyl |
| (7) | (methacrylate-glyceryl-naphthoate-propoxy-siloxane structure) $Si(O_{1/2})_a(C_2H_5)_b$ | $CH_3$ | $C_2H_5$ | 1-naphtyl |

-continued

| No. | Siloxane unit | A | R¹ | R² |
|---|---|---|---|---|
| (8) | [structure] | $CH_3$ | $C_2H_5$ | 4-tert.-butyl-1-phenyl |
| (9) | [structure] | $CH_3$ | $C_2H_5$ | n-undecanyl |
| (10) | [structure] | H | $C_2H_5$ | 1-naphtyl |
| (11) | [structure] | H | $C_2H_5$ | 4-tert.-butyl-1-phenyl |

| No. | Siloxane unit | A | $R^1$ | $R^2$ |
|---|---|---|---|---|
| (12) | | H | $C_2H_5$ | n-undecanyl |
| (13) | 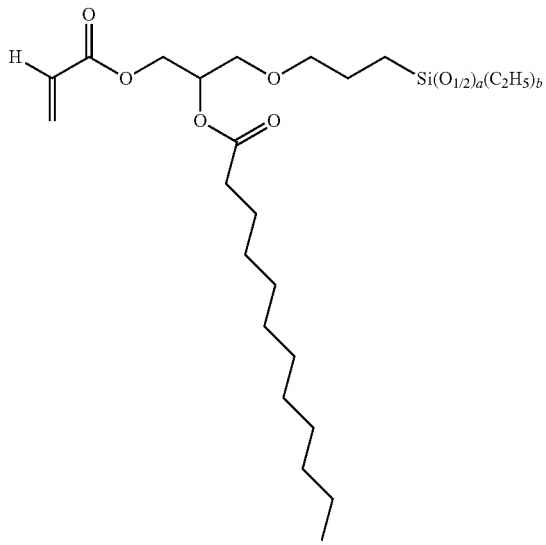 | $CH_3$ | $C_3H_7$ | 1-naphtyl |
| (14) | 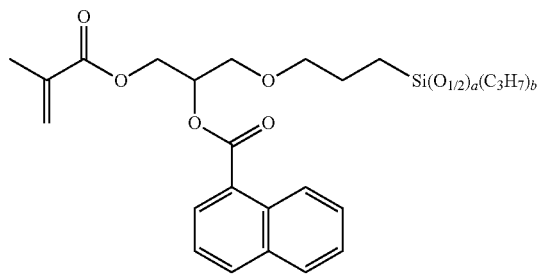 | $CH_3$ | $C_3H_7$ | 4-tert.-butyl-1-phenyl |
| | 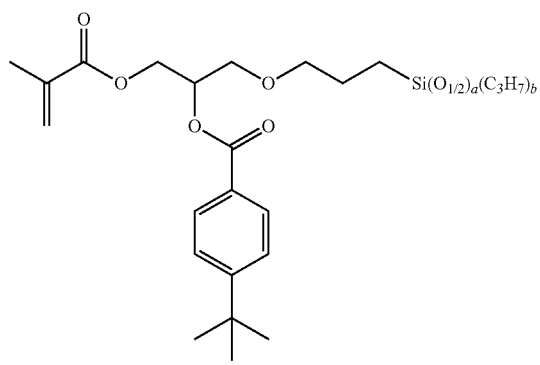 | | | |

| No. | Siloxane unit | A | R¹ | R² |
|---|---|---|---|---|
| (15) | | CH₃ | C₃H₇ | n-undecanyl |
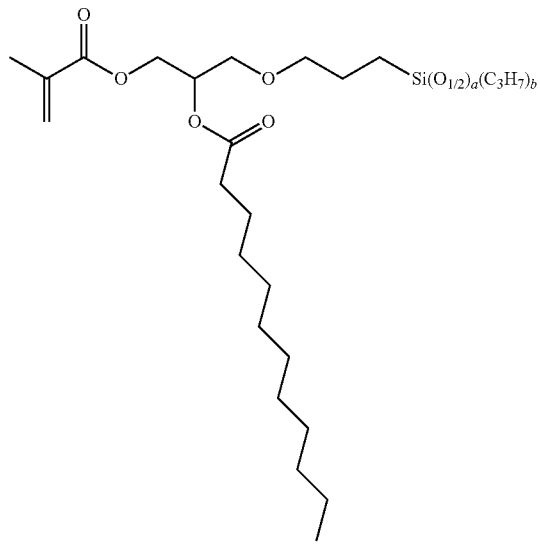
| | | | | |
|---|---|---|---|---|
| (16) | | H | C₃H₇ | 1-naphtyl |
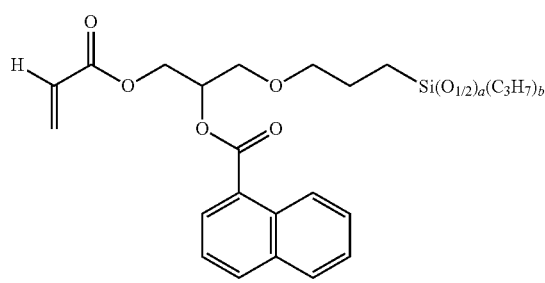
| | | | | |
|---|---|---|---|---|
| (17) | | H | C₃H₇ | 4-tert.-butyl-1-phenyl |
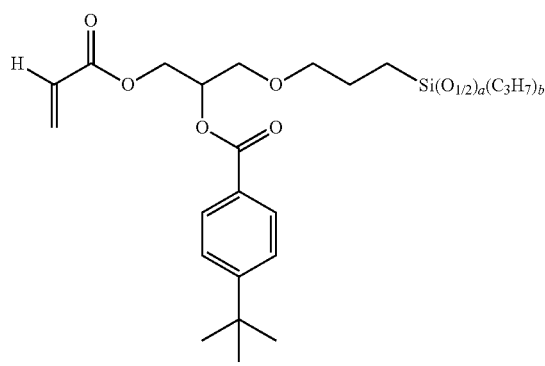

-continued
| No. | Siloxane unit | A | R¹ | R² |
|---|---|---|---|---|
| (18) | | H | $C_3H_7$ | n-undecanyl |
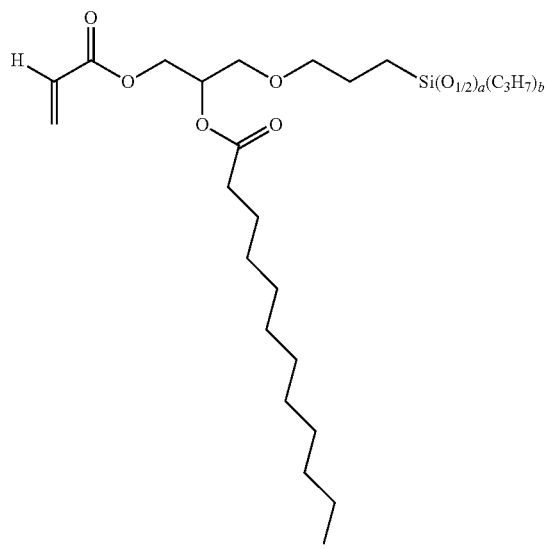
| | | | | |
|---|---|---|---|---|
| (19) | | $CH_3$ | $C_4H_9$ | 1-naphtyl |
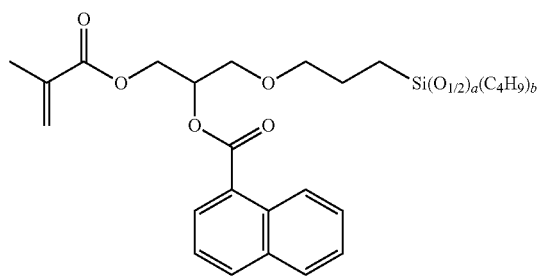
| | | | | |
|---|---|---|---|---|
| (20) | | $CH_3$ | $C_4H_9$ | 4-tert.-butyl-1-phenyl |
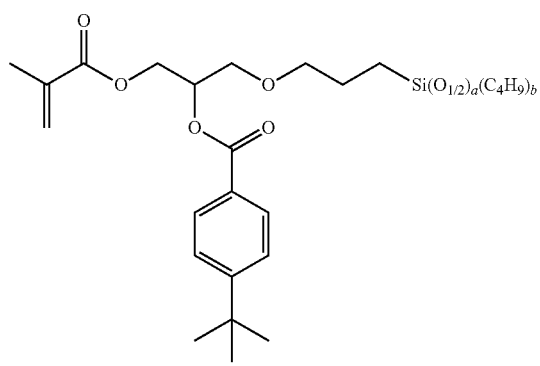

-continued
| No. | Siloxane unit | A | R¹ | R² |
|---|---|---|---|---|
| (21) | | CH$_3$ | C$_4$H$_9$ | n-undecanyl |
| (22) | | H | C$_4$H$_9$ | 1-naphtyl |
| (23) | | H | C$_4$H$_9$ | 4-tert.-butyl-1-phenyl |
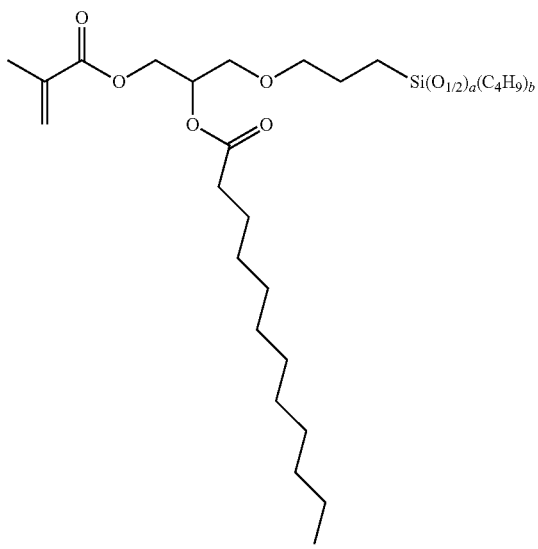
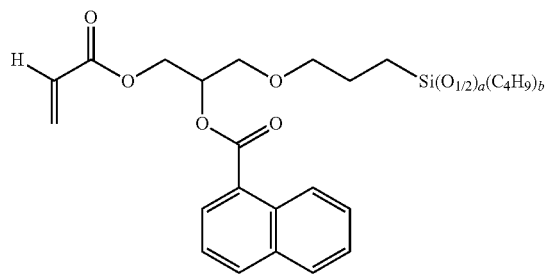
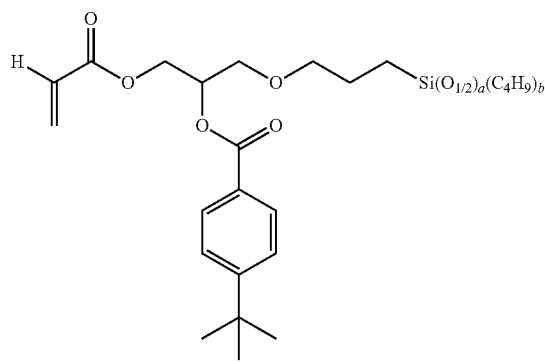

| No. | Siloxane unit | A | $R^1$ | $R^2$ |
|---|---|---|---|---|
| (24) | [structure: acrylate-O-CH2-CH(O-C(=O)-long alkyl chain)-CH2-O-CH2CH2CH2-Si(O_{1/2})_a(C_4H_9)_b] | H | $C_4H_9$ | n-undecanyl | wherein
$b$ denotes 0, 1 or 2 and
$a$ denotes 3-b.

The invention also relates to mixtures comprising two, three or more than three different polysiloxane compounds according to the invention (as defined above, preferably as defined above as preferred). Particularly preferably the invention relates to mixtures comprising two, three or more than three different polysiloxane compounds according to the invention (as defined above, preferably as defined above as preferred) for use in a therapeutic procedure, preferably as a polymerisable component of a curable dental material. Quite particularly preferably the invention relates to mixtures comprising two, three or more than three different polysiloxane compounds according to the invention (as defined above, preferably as defined above as preferred) for specific use in a therapeutic procedure for temporary or permanent filling of a dental cavity
or
in a therapeutic procedure as a
- dental filling material,
  - dental lining material (dental underfilling material),
  - dental adhesive (bonding),
  - as a flowable composite material (flow material),
  - as a fissure sealant.
  - as a crown material,
  - as an inlay and/or onlay,
  - as a bridge material
  - and/or as a core build-up material.

The invention also relates to a curable dental material comprising one or more than one polysiloxane compound according to the invention (as defined above, preferably as defined above as preferred) and one or more than one compound different from the polysiloxane compound according to the invention (as defined above, preferably as defined above as preferred). More details about compounds different from the polysiloxane compound according to the invention are stated below in the present text. That stated in connection with polysiloxane compounds according to the invention applies by analogy to the curable dental material.

In preferred cases the curable dental material according to the invention comprises a mixture according to the invention (as defined above, preferably as defined above as preferred) comprising two, three or more than three different polysiloxane compounds according to the invention (as defined above, preferably as defined above as preferred).

Preference is for a curable dental material (as described above), further comprising one, two or more than two or all substances from the group consisting of.
- dental organic filler particles, which are preferably radiopaque and/or nanoscale,
- dental inorganic filler particles which are preferably radiopaque and/or nanoscale,
- dental organic surface-modified inorganic filler particles, which are preferably radiopaque and/or nanoscale,
- rheological agents,
- polymerisation initiators, preferably photoinitiators,
- chemical compounds as catalysts or components of catalyst systems.
- colourants, preferably dye pigments,
- stabilisers, in particular daylight stabilisers.
- inhibitors,
- activators,
- molecular weight modifiers,
- preservatives,
- surface-active substances,
- microbicides, preferably bactericides,
- organic, preferably radically polymerisable monomers, which are not polysiloxanes according to the invention, preferably for conversion with the polysiloxane compound according to the invention,
- organic polymers and oligomers and compounds with high molecular weights, preferably plasticisers,
- thickeners and
- dental medicinal products.

Preferred dental filler particles for a curable dental mixture according to the invention are organic filler particles or inorganic filler particles or mixtures of organic and inorganic filler particles. Particular preference is for inorganic filler particles, preferably radiopaque filler particles.

The dental inorganic filler particles can all be chemically identical or be used as mixtures of chemically different dental inorganic filler particles.

The dental inorganic filler particles are preferably selected from the group consisting of mixed oxides of $SiO_2$, $ZrO_2$ and/or $TiO_2$, fumed silica, precipitated silica, barium silicate glasses, barium fluorosilicate glasses, strontium silicate glasses, strontium borosilicate glasses, Li/Al-silicate glasses, barium glasses, calcium silicates, sodium aluminium silicates, fluoro-aluminium-silicate glasses, oxides of aluminium or silicon, zeolites, apatite, zirconium silicates and hardly soluble metal salts such as barium sulphate or calcium fluoride. Preferably used radiopaque filler particles are regularly inorganic filler particles and are preferably selected from the group consisting of fluorides of the rare earth metals (such as ytterbium fluoride and yttrium trifluoride) and strontium hexafluorozirconate. A particularly preferred radiopaque inorganic filler is ytterbium fluoride. For certain applications a mixture of radiopaque filler particles (preferably as described above) and inorganic filler particles, which do not themselves contribute to x-ray opacity, is preferred. Particular preference here is for barium silicate glasses and/or barium fluoride silicate glasses.

In a curable dental material according to the invention particularly preferably dental filler particles are used, which have a refractive index ranging from 1.46 to 1.56, preferably ranging from 1.48 to 1.54
and/or for which the following applies:
the amount of the difference in refractive index between
the refractive index of the dental filler particles taken as a whole and the refractive index of the polysiloxane compound(s) according to the invention taken as a whole
ranges from 0.01 to 0.04.

If for example the polysiloxane compound(s) according to the invention taken as a whole has or have a refractive index of 1.50 and the dental filler particles taken as a whole a refractive index of 1.51, the difference is 0.01.

Preference is for the use of surface-modified inorganic filler particles. Preferably used surface-modified inorganic filler particles are obtained by surface modification with a silane such as methacryloxypropyltrimethoxysilane.

Organic filler particles comprise or consist of, for example, one or more compounds selected from the group consisting of polyvinyl acetate and copolymers of polyvinyl acetate with one or more polymerisable compounds, polystyrene, polyethylene, polypropylene, waxes such as polyethylene wax, polybutylene, polybutadiene, copolymers of butadiene and styrene, polyacrylonitrile, resins such as rosin resin or hydrocarbon resins, poly(meth)acrylic acid esters, i.e. conversion products of poly(meth)acrylic acid with linear or branched aliphatic, aromatic or cycloaliphatic alcohols such as methanol, ethanol, propanol, isopropanol, the isomers of butanols and higher homologues of the stated alcohols with up to 22 carbon atoms, cyclohexanol, benzyl alcohol and similar, poly dialkyl maleinates such as dibutyl maleinate and copolymers thereof and silyl group-containing polymers such as polyvinyl silanes or copolymers of vinyl silane with one or more of the stated monomers.

Preferred curable dental materials according to the invention (as defined above, preferably as defined above as preferred) are light curable (photocurable). The crosslinking/polymerisation of the polysiloxane compound according to the invention in such dental materials according to the invention then regularly takes place through the effect of light of certain wavelengths and in the presence of photoinitiators. Examples of photoinitiators include compounds having just a photo-sensitising effect and combinations of sensitisers and accelerators.

Examples of photo-sensitisers are alpha-diketone, benzoin alkyl ethers, thioxanthones, benzophenones, acylphosphinoxides, acetophenones, ketals, titanocenes, sensitising dyes, and so on. The sensitisers can be applied alone or in combination. Specific examples of the various classes can be found for example in DE 10 2006 019 092 A1 and DE 39 41 629 C2, which by way of reference are a component part of this application.

Examples of accelerators, used together with sensitisers, are tertiary amines, secondary amines, barbituric acids, tin compounds, aldehydes and sulphur compounds. Specific examples of the various classes can be found in DE 10 2006 019 092 and DE 39 41 629 C2, which by way of reference are a component part of this application.

Further suitable initiators and initiator combinations are described in DE 601 16 142 T2, which by way of reference is a component part of this application.

Photoinitiators preferably used in the context of the invention are characterised in that, through the absorption of light in the wavelength range of 300 nm to 700 nm, preferably of 350 nm to 600 nm and particularly preferably of 380 nm to 500 nm, if necessary in combination with one or more coinitiators, they can bring about the curing (crosslinking/polymerisation) of a curable dental material according to the invention or to be applied or used according to the invention.

Further preferred curable dental materials according to the invention (as defined above, preferably as defined above as preferred) can be cured by chemical curing. For this various initiators for chemical curing are known to the person skilled in the art. In this regard by way of example reference is made to the disclosure in EP 1 720 506 A1.

In many cases a curable dental material according to the invention is preferred which is both light curable and also chemically curable. These preferred dual-curing dental materials comprise a combination of photoinitiators and initiators for chemical curing. The above statements on preferred initiators apply by analogy.

Preferred light-curable dental materials according to the invention (as defined above, preferably as defined above as preferred, including the dual-curing dental materials according to the invention), preferably contain one or more inhibitors (also referred to as stabilisers). These are normally added to avoid a spontaneous polymerisation. They react with prematurely occurring radicals, which are trapped, preventing premature polymerisation. This increases the storage stability of the preferred light-curable dental materials (or of the dual-curing dental materials). Inhibitors to be used by preference are phenol derivatives such as hydroquinone monomethylether (HQME) or 2,6-di-tert.butyl-4-methylphenol (BHT). Further inhibitors to be used by preference such as tert.-butylhydroxyanisol (BHA), 2,2 diphenyl-1-picrylhydrazyl-, galvinoxyl-, triphenylmethyl radicals, 2,3,6,6,tetramethylpiperidine-1-oxyl radicals (TEMPO) and derivatives of TEMPO or phenothiazines and derivatives of these compounds are described in EP 0 783 880 B1, which by way of reference is a component part of this application. Alternative preferred inhibitors are indicated in DE 101 19 831 A1 and in EP 1 563 821 A1, which by way of reference are a component part of this application.

Preferred light-curable dental materials according to the invention (as defined above, preferably as defined above as preferred, including the dual-curing dental materials according to the invention), preferably contain one or more organic, preferably radically polymerisable monomers, in particular monofunctional and/or polyfunctional methacrylates, which can be used alone or in mixtures. Examples of these compounds are alkyl methacrylates such as for example methyl methacrylate, ethyl methacrylate, propyl methacrylate, butyl methacrylate, etc., alkylene glycol dimethacrylates and polyethylene glycol dimethacrylates such as for example tetraethylene glycol dimethacrylate, triethylene glycol dimethacrylate, diethylene glycol dimethacrylate, ethylene glycol dimethacrylate, butane diol dimethacrylate, hexane diol dimethacrylate, decane diol dimethacrylate, dodecane diol dimethacrylate, the mono-, di-, tri-, tetra- or penta-methacrylate polyvalent alcohols such as for example trimethylolpropane dimethacrylate, dipentaerythritol penta methacrylate, dimethylolpropane trimethacrylate, neopentylglycol methacrylate, the methacrylates of alkoxylated, (ethoxylated, propoxylated, etc.) glycerine, trimethylolpropane, pentaerythritol, dipentaerythritol, dimethylolpropane, and so on, and their technical mixtures, bisphenol-A-dimethacrylate, 2,2-bis[4(3-methacryloxy-2-hydroxypropoxy)-phenyl]propane (bis-GMA) and the reaction products of isocyanates, in particular di- and/or triisocyanates and OH-group-containing methacrylates and the methacrylates of the radically polymerisable TCD (tricyclodecane)derivatives such as TCD-di-HEMA and/or TCD di-HEA and polymerisable compounds, as known from EP 2 436 668 B1.

Preferred curable dental materials according to the invention (as defined above, preferably as defined above as preferred) are characteristically shaded, preferably a tooth shade that is included in the "VITA classical A1-D4 shade guide"; such shades are designated A1-A4 (reddish-brownish), B1-B4 (reddish-yellowish), C1-C4 (greyish shades) and D2-D4 (reddish-grey). Preferred shades can be adjusted using colourants, preferably dye pigments.

As already described above, the curable dental material according to the invention can be cured. The invention thus also relates to a cured dental material, obtainable from a curable dental material according to the invention (as defined above, preferably a curable dental material as defined above as preferred) by means of polymerisation of the polysiloxane compound contained in the dental material and possibly further polymerisable components contained in the dental material. The polymerisation or crosslinking takes place by means of the organically polymerisable double bonds contained in the (meth)acrylate groups.

That stated in connection with preferable embodiments of polysiloxane compounds according to the invention and curable dental materials according to the invention applies by analogy to the cured dental materials according the invention.

An important aspect of the invention relates to a polysiloxane compound according to the invention (as defined above, preferably a polysiloxane compound as defined above as preferred) or a curable dental material according to the invention (as defined above, preferably a curable dental material as defined above as preferred) or cured dental material according to the invention (as defined above, preferably a cured dental material as defined above as preferred) for use in a therapeutic procedure, wherein a polysiloxane compound according to the invention is preferably used as a polymerisable component of a curable dental material.

Particular preference in this respect is for the specific use of the polysiloxane compound according to the invention (polysiloxane compounds as defined above, preferably polysiloxane compounds as defined above as preferred) or of the curable dental material according to the invention (curable dental materials as defined above, preferably curable dental materials as defined above as preferred) or of the cured dental material according to the invention (as defined above, preferably a cured dental material as defined above as preferred) in a therapeutic procedure for temporary or permanent filling of a dental cavity or in a therapeutic procedure as
dental filling material.
dental lining material (dental underfilling material),
dental adhesive (bonding),
as a flowable composite material (flow material),
as a fissure sealant,
as a crown material,
as an inlay and/or onlay,
as a bridge material
and/or as a core build-up material.

In some preferred therapeutic procedures the curable dental material according to the invention is applied as a fissure sealant and/or for sealing carious lesions. In these and in other cases the curable dental material according to the invention preferably comprises one or more fluoridating substances, preferably substances releasing sodium fluoride and/or amino fluorides.

Our own investigations have shown that the polysiloxane compounds according to the invention (as defined above, preferably polysiloxane compounds as defined above as preferred) and the curable dental material according to the invention (as defined above, preferably curable dental materials defined above as preferred) lead to exceptional results in the abovementioned specific applications.

The invention further relates to a method for preparing a polysiloxane compound (as defined above, preferably polysiloxane compounds as defined above as preferred), with the following steps:
preparing or providing an intermediate polysiloxane compound comprising
($A_P$) one, two, three or more than three in each case structurally identical first intermediate siloxane units selected from the group consisting of siloxane units of the general formula ($I_P$)

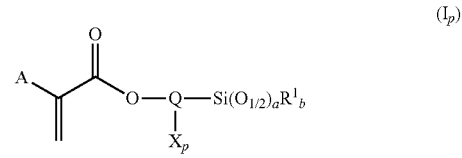

wherein for the structural units A, Q, $X_P$ and $R^1$ in each of the structurally identical first siloxane units independently of one another the following applies:
A denotes H or $CH_3$,
Q denotes a link group bearing the substituent $X_P$,
$R^1$ denotes an alkyl radical with a total of 1 to 4 carbon atoms
and
$X_P$ for a reactive group
wherein
b denotes 0, 1 or 2 and
a denotes 3-b,
conversion of the intermediate polysiloxane compound in one or more steps through reaction of the reactive group $X_P$, so that the polysiloxane compound according to the invention is formed (a polysiloxane compound as defined above, preferably a polysiloxane compound as defined above as preferred).

Methods for the preparation of an intermediate polysiloxane compound are known to a person skilled in the art. In particular, preparation takes place through condensation reactions of existing or previously synthesised silanes (see for example DE 4416857 C1). Here in a first step the monomeric silane unit is first prepared (see example Diagram (c), wherein A denotes $CH_3$ or H, reactant 1: (meth)acrylic acid, reactant 2: 3-glycidyloxypropyl-methyldiethoxysilane, reaction product: monomeric silane unit). The reactive group in the monomeric silane unit is often a hydroxy group.

reactive group. These reactive hydroxy groups are converted in a subsequent reaction step, e.g. with carboxylic acid derivatives, such that polysiloxane compounds according to the invention are obtained (see the following example Diagrams (f), (g) and (h), wherein respectively A denotes $CH_3$ or H and $O_{1/2}$ for the oxygen link to the next silicon atom in the polysiloxane compound according to the invention). Diagrams (f), (g) and (h) show by way of example the conversion of a reaction product (intermediate polysiloxane compound) according to example Diagram (d) with various acid chloride bonds.

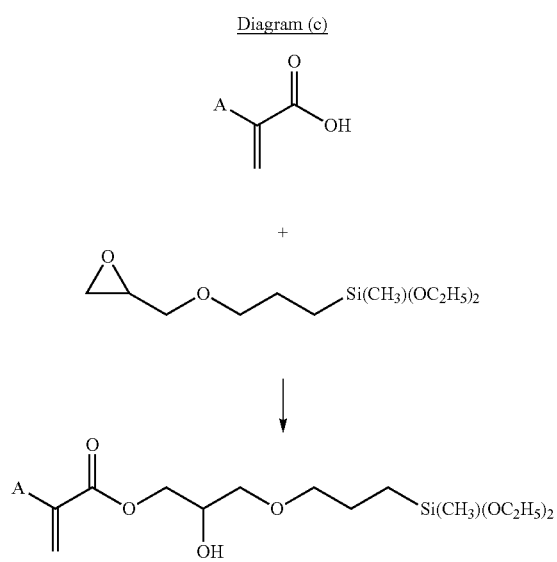

Diagram (c)

The prepared monomeric silane units are then condensed, in order to obtain an intermediate polysiloxane compound (see schematic example Diagram (d)), wherein A denotes $CH_3$ or H and $O_{1/2}$ for the oxygen link to the next silicon atom in the intermediate polysiloxane compound).

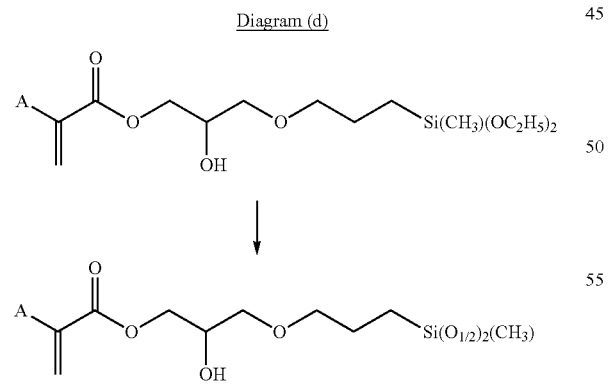

Diagram (d)

Monomeric silane units prepared according to example Diagram (c) can also be converted with other, structurally diverse monomeric silane units (co-condensed).

A reaction product formed according to example Diagram (d) is an intermediate polysiloxane compound within the meaning of the present text and has one or more free polar hydroxy groups (reactive hydroxy groups) as an exemplary

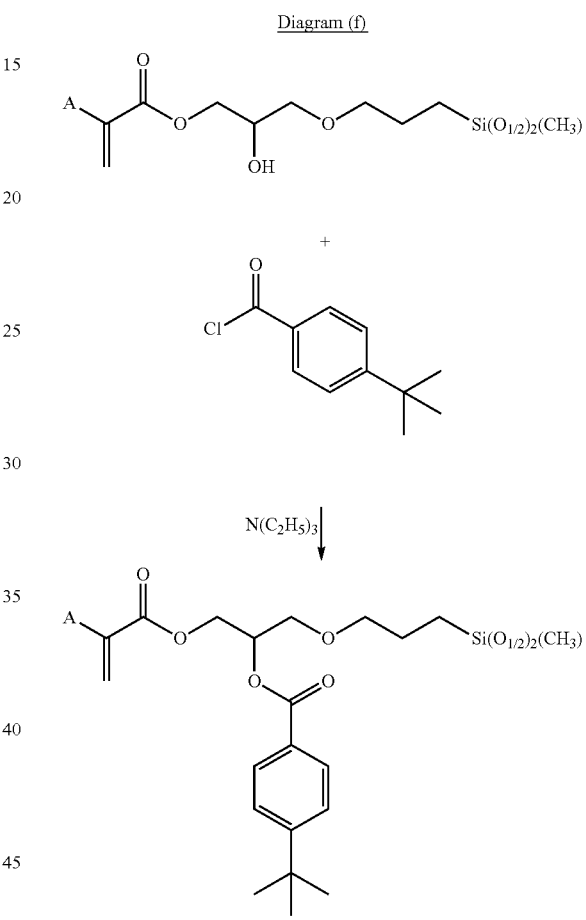

Diagram (f)

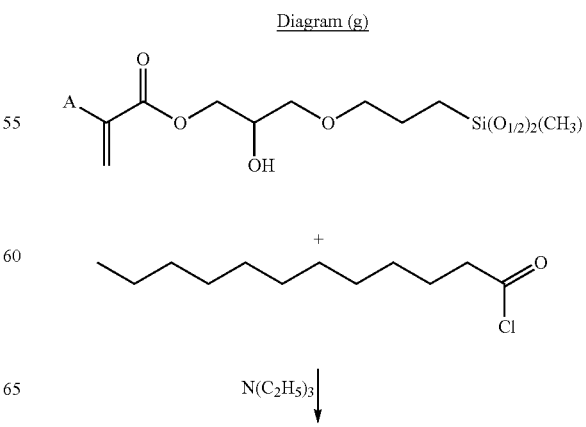

Diagram (g)

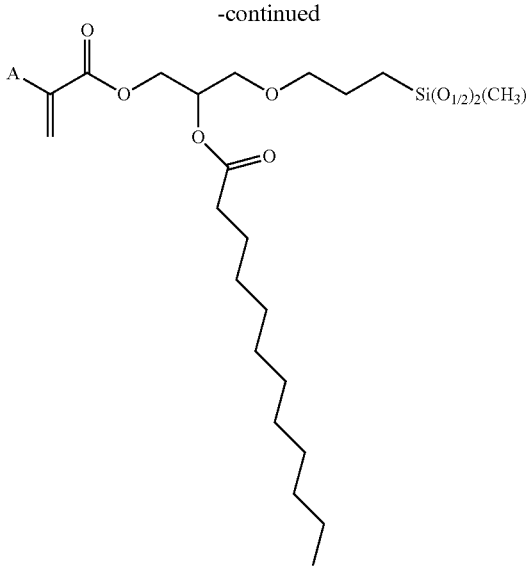

Diagram (h)

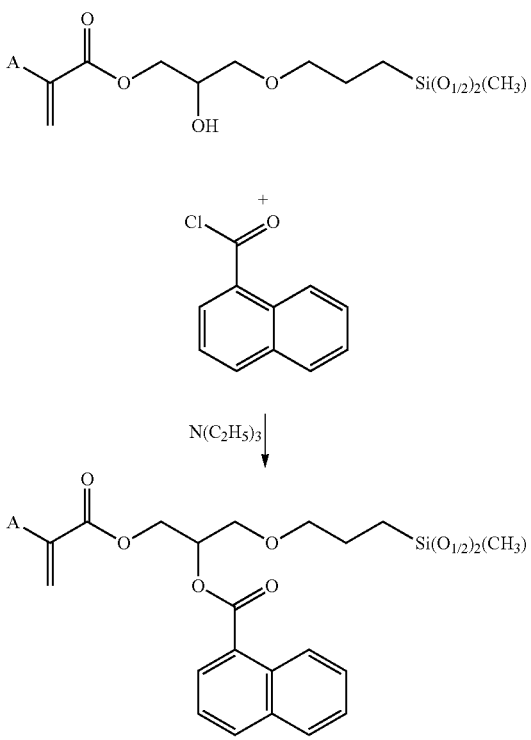

The invention also relates to a kit, comprising
one, two or more than two curable dental materials according to the invention (as defined above, preferably curable dental materials defined above as preferred)
and/or
one, two or more than two base pastes and one, two or more than two catalyst pastes, wherein the one base paste or the two or more than two base pastes in each case and independently of one another comprises or comprise one or more than one polysiloxane compound according to the invention (as defined above, preferably as defined above as preferred).

That stated in connection with the polysiloxane compounds according to the invention or curable dental materials applies by analogy to the kit according to the invention.

Preference is for a kit according to the invention (as defined above), wherein
the one or the two or more than two curable dental materials according to the invention (as defined above, preferably curable dental materials defined above as preferred)
or
the one or the two or more than two base pastes
has or have a shade that is included in the "VITA classical A1-D4 shade guide".

Particular preference is for a kit according to the invention (as defined above, preferably as described above as preferred) comprising
two or more than two curable dental materials according to the invention (as defined above, preferably curable dental materials defined above as preferred)
and/or
two or more than two base pastes and one, two or more than two catalyst pastes, wherein the two or more than two base pastes in each case and independently of one another comprises or comprise one or more than one polysiloxane compound according to the invention (as defined above, preferably as defined above as preferred), wherein
the two or more than two curable dental materials according to the invention (as defined above, preferably curable dental materials defined above as preferred)
or
the two or more than two base pastes
in each case have a shade included in the "VITA classical A1-D4 shade guide", wherein the respective shades are preferably different.

The kit according to the invention (as defined above, preferably as described above as preferred) also comprises one, more than one or all the items selected from the group consisting of
one, two or more than two bondings,
one, two or more than two etchants,
one or more than one shade guide,
one or more than one brush,
one or more than one material with a viscosity, that differs from the viscosity or viscosities of the curable dental material or dental materials according to the invention and/or from the viscosity (viscosities) of the base paste(s) or the catalyst paste(s), preferably one or more than one flow-material.

The invention further relates to a method for preparing a curable dental material according to the invention (a curable dental material as defined above, preferably a curable dental material as defined above as preferred) with the following steps:
providing or preparing one or more polysiloxane compounds according to the invention (polysiloxane compounds as defined above, preferably as defined above as preferred),
providing or preparing one, more or all substances as defined above as substances, preferably as defined above as preferred substances,
preparing a single-component or multi-component system comprising the provided or prepared polysiloxane compound(s) according to the invention and the provided or prepared substance(s) and optionally, additional substances,
wherein preferably in multi-component systems the substances triggering a polymerisation are distributed over separate components such that a polymerisation of the polysiloxane compounds is triggered through mixing of said components.

In methods according to the invention for preparing curable dental materials, in which a curable dental material is prepared, which is curable through light curing, the preparation of a single-component system is preferred. In this case the curable dental material contains in the individual components in particular all the ingredients necessary for light curing and a polymerisation is initiated by irradiation with light of a defined wavelength (for light curing of curable dental materials see above in the text). The single-component system is preferably used as a part of the kit according to the invention (as defined above in the text).

In methods according to the invention for the preparation of curable dental materials, in which a curable dental material is prepared which (a) is curable by light curing and by chemical curing (dual-curing) or (b) is curable only by chemical curing, the preparation of a multi-component system is preferred. Curable dental materials, which are curable by chemical curing, are preferably prepared as a two-component system, so that the substances triggering a polymerisation (e.g. polymerisation initiators, catalysts for chemical curing or ingredients of catalysts for chemical curing, etc.) and the polymerisable compounds are present in separate components and only by mixing the separate components does a polymerisation take place. Dual-curing dental materials are preferably similarly produced as two-component systems. Here the substances which trigger a polymerisation by chemical curing are preferably present in at least one separate component of the multi-component system. The multicomponent system (preferably the two-component system) is preferably used as part of a kit according to the invention (as defined above in the text). In this case the polymerisable compounds, preferably the polymerisable compounds according to the invention, are preferably present in the base paste(s), and the substances triggering a chemical curing in the catalyst paste(s).

The invention also relates to a method for preparing a cured dental material (a cured dental material as defined above, preferably a cured dental material as defined above as preferred), with the following steps:

providing or preparing a curable dental material according to the invention (as defined above, preferably a curable dental material as defined above as preferred), polymerisation of the polysiloxane compound contained in the dental material according to the invention and possibly further polymerisable components contained in the dental material.

The polymerisation or crosslinking of the polysiloxane compound (preferably a polysiloxane compound according to the invention as defined above, preferably as designated above as preferred) takes place by means of the organically polymerisable double bonds of the corresponding polysiloxane compound contained in the (meth)acrylate groups. Preferably in a method according to the invention for preparation of a cured dental material the polymerisation of the polysiloxane compound contained in the dental material according to the invention and if necessary further polymerisable ingredients contained in the dental material, is carried out in such a way that a workpiece suitable for further processing is obtained, preferably a milling block (milling blank) or a blank. Particularly preferably cuttable milling blanks are obtained. Cuttable milling blanks are suited in particular to the preparation of customised dental components in the area of medicine and in particular in the area of dentistry. Preferred dental components are replacement materials for teeth and bone structures; particularly preferred dental components are selected from the group consisting of restorations, replacements, inlays, onlays, veneers, full crowns, partial crowns, bridges, implants, artificial teeth, train tracks, retainers, braces and pins. The workpieces suitable for further processing, preferably the milling blocks (milling blanks), blanks and cuttable milling blanks, preferably exist in any desired form and/or size, particularly preferably in the form of a cylinder, bar, cube, polyhedron, ovoid or as a plate. The three-dimensional form of the abovementioned workpieces suitable for further processing is preferably selected so that workpieces suitable for further processing are obtained, which are approximated or adapted to the shape/design of the dental components to be made from them.

It is preferred that the cured dental material according to the invention, which is preferably present as a suitable workpiece, particularly preferably as a milling block or blank, is further processed in an additional step. Preference is for a method according to the invention for preparation of a cured dental material (as defined above) with the additional step of:

processing of the cured dental material obtained by polymerisation of the polysiloxane compound contained in the dental material according to the invention together with any other polymerisable components contained in the dental material preferably of the milling block or of the blank, so that a dental component or a precursor to a dental component is obtained, wherein the method is preferably a chip removal machining process, wherein the chip removal machining process preferably comprises one or more methods, selected from the group consisting of turning, milling, boring, sawing, filing, cutting and grinding.

Particular preference is for a method according to the invention for preparation of a cured dental material (as defined above, preferably as designated above as preferred), wherein the processing, preferably the chip removal machining process (preferably the chip removal machining processes designated above as particularly preferred) comprises computer-aided design (CAD), and/or computer-aided manufacturing (CAM). Once processing has taken place the cured dental material is present formed as a dental component or as a precursor to a dental component. Preferred dental components are selected from the group consisting of restorations, replacements, inlays, onlays, veneers, full crowns, partial crowns, bridges, implants, artificial teeth, splints, retainers, braces and pins.

It transpires that the cured dental materials according to the invention in many applications are particularly well-suited to CAD/CAM-assisted chip removal machining processes. The invention therefore also relates to the use of a cured dental material according to the invention (as defined above, preferably a cured dental material as described above as preferred, preferably a milling block or blank) for the preparation of dental components or precursors to dental components, preferably for the preparation of dental components or precursors to dental components by means of computer-aided design (CAD) and/or computer-aided manufacturing (CAM).

Finally, the invention also relates to a dental treatment method with the following step:

Application of a curable dental material according to the invention (as defined above, preferably a curable dental material as defined above as preferred)

to the tooth substance or the dental tissue of a patient or to a dental restoration.

The following examples serve to illustrate the invention.

A) PREPARATION AND PROPERTIES OF POLYSILOXANE COMPOUNDS

1.) Example Synthesis of an Intermediate Polysiloxane Compound with Reactive Polar Group (See EP 1 685 182 B1) (Polysiloxane A)

1.1) Synthesis of a Monomeric Silane Unit (See EP 1 685 182 B1, Example 3):

To the pre-mixed material of 100 g (0.402 mol) 3-glycidyloxypropyldiethoxymethylsilane under dry atmosphere (oxygen) an addition catalyst, BHT as the stabilizer and then 38.05 g (0.442 mol) methacrylic acid were added in drops with agitation at approximately 80° C. (approximately 24 hours) (see Diagram (c) top, or paragraph [0048] in EP 1 685 182 B1). The conversion was monitored through the decrease in the carboxylic acid concentration by means of acid titration and the epoxy conversion by means of Raman spectroscopy/epoxy titration. The bands characteristic of the epoxy group were detected in the Raman spectrum at 1256 cm$^{-1}$. The epoxy or carboxylic acid conversion was >99% or >88% (a result of the excess carboxylic acid).

1.2) Hydrolysis or Condensation or the Monomeric Silane Unit to an Intermediate Polysiloxane Compound (Polysiloxane A) (See Diagram (d) Top, or EP 1 685 182 B1, Example 6):

Following addition of ethyl acetate (1 000 ml/mol monomeric silane unit) and H$_2$O for hydrolysis with HCl as catalyst to the synthesised monomeric silane unit agitation took place at 30° C. The progress of the hydrolysis was monitored by water titration. The working up took place after a number of days' agitation at 30° C. through repeated extraction with aqueous NaOH and subsequent extraction with water and filtration via a hydrophobic filter. Following addition of BHT rotary evaporation initially took place at 40° C. and then the solvent residues (e.g. water and alcohol residues) were extracted under vacuum by means of an oil pump, in order to remove the alcohol and water residues. The result was a liquid resin with a viscosity of 4.5 Pa·s at 25° C. (highly dependent upon the precise hydrolysis and working up conditions).

The intermediate polysiloxane compound referred to as polysiloxane A serves in the following on the one hand as a reference compound in a comparison of physical properties (see Table 2 below) and on the other as a starting compound for further conversion to a polysiloxane compound according to the invention.

2) Preparation of Polysiloxane Compounds According to the Invention (Polysiloxanes B, C, D, E, and F):

2.1) Preparation of a Polysiloxane Compound According to the Invention (Polysiloxane B) by Converting Polysiloxane a with Naphthoyl Chloride:

To a premixed material of 15 mmol polysiloxane A and 1.1 eq triethylamine in toluene under dry atmosphere and ice cooling (4° C.) a solution of 1.1 eq. naphthoyl chloride in toluene was slowly added in drops. Once addition was complete the solution was agitated at room temperature. The conversion was monitored via the reduction in the band characteristic of the OH group by IR spectroscopy; the band characteristic of the OH group was detected under IR at 3200-3400 cm$^{-1}$. For working up the solution was initially extracted with 1M HCl and then washed twice with water. Following drying of the organic phase over magnesium sulphate and removal of the solvent under vacuum a slightly yellowy flowable resin with a viscosity of 17.5 Pa·s at 25° C. was obtained. Table 2 provides a comparison of physical properties.

2.2) Preparation of a Polysiloxane Compound According to the Invention (Polysiloxane C) by Converting Polysiloxane a with Tert-Butylbenzoyl Chloride:

To a pre-mixed material of 15 mmol polysiloxane A and 1.1 eq triethylamine in toluene under dry atmosphere and ice cooling (4° C.) a solution of 1.1 eq. tert-butylbenzoyl chloride in toluene was slowly added in drops. Once addition was complete the solution was agitated at room temperature. The conversion was monitored via the reduction in the band characteristic of the OH group by IR spectroscopy; the band characteristic of the OH group was detected under IR at 3200-3400 cm$^{-1}$. For working up the solution was initially extracted with 1M HCl and then washed twice with water. Following drying of the organic phase over magnesium sulphate and removal of the solvent under vacuum a slightly yellowy flowable resin with a viscosity of 13.5 Pa·s at 25° C. was obtained. Table 2 provides a comparison of physical properties.

2.3) Preparation of a Polysiloxane Compound According to the Invention (Polysiloxane D) by Conversion of Polysiloxane a with n-Dodecanoyl Chloride:

To a pre-mixed material of 15 mmol polysiloxane A and 1.1 eq. triethylamine in toluene under dry atmosphere and ice cooling (4° C.) a solution of 1.1 eq. n-dodecanoyl chloride in toluene was slowly added in drops. Once addition was complete the solution was agitated at room temperature. The conversion was monitored via the reduction in the band characteristic of the OH group by IR spectroscopy; the band characteristic of the OH group was detected under IR at 3200-3400 cm$^{-1}$. For working up the solution was initially extracted with 1M HCl and then washed twice with water. Following drying of the organic phase over magnesium sulphate and removal of the solvent under vacuum a slightly yellowy flowable resin with a viscosity of 1.5 Pa·s at 25° C. was obtained. Table 2 provides a comparison of physical properties.

2.4) Preparation of a Polysiloxane Compound (Amide) According to the Invention (Polysiloxane E) by Conversion of Polysiloxane a with (i) Para-Toluenesulfonyl Chloride and Subsequently with (ii) Naphthalene-1-Carboxamide (See Diagram (m)):

A solution of 16.5 mmol (1.1 eq.) para-toluenesulfonyl chloride in 50 ml of a mixture of acetone/toluene (volume ratio: 1:1) was mixed under ice cooling (4° C.) with 16.5 mmol triethylamine (1.1 eq.). The resulting mixture was subsequently mixed with 15 mmol polysiloxane A (1.0 eq.). Once mixing was complete the resulting clear solution was continually agitated at 4° C. for one hour. Afterwards, a solution of 1.1 eq. naphthalene-1-carboxamide and 1.1 eq. triethylamine in 5 ml acetone/toluene (volume ratio: 1:1) was slowly added in drops. The resulting solution was heated to 75° C. and said temperature was maintained for 3 hours.

In a next step the solution was washed with water three times and the organic phase was dried over magnesium sulphate. Following removal of the solvent under vacuum a slightly yellowy flowable (liquid) resin with a viscosity of 24 Pa·s at 25° C., a refractive index n$_D$ of 1.52, and a shrinkage of 3.6% was obtained. Table 2 provides a comparison of physical properties.

Diagram (m)

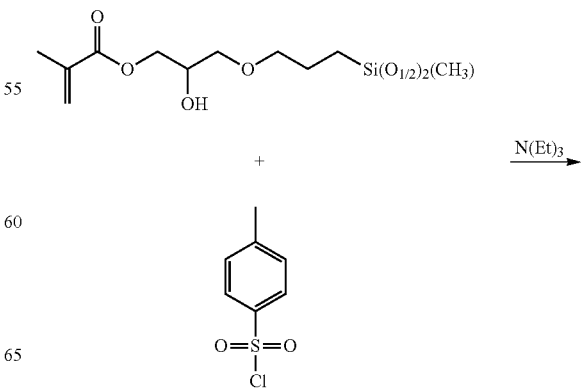

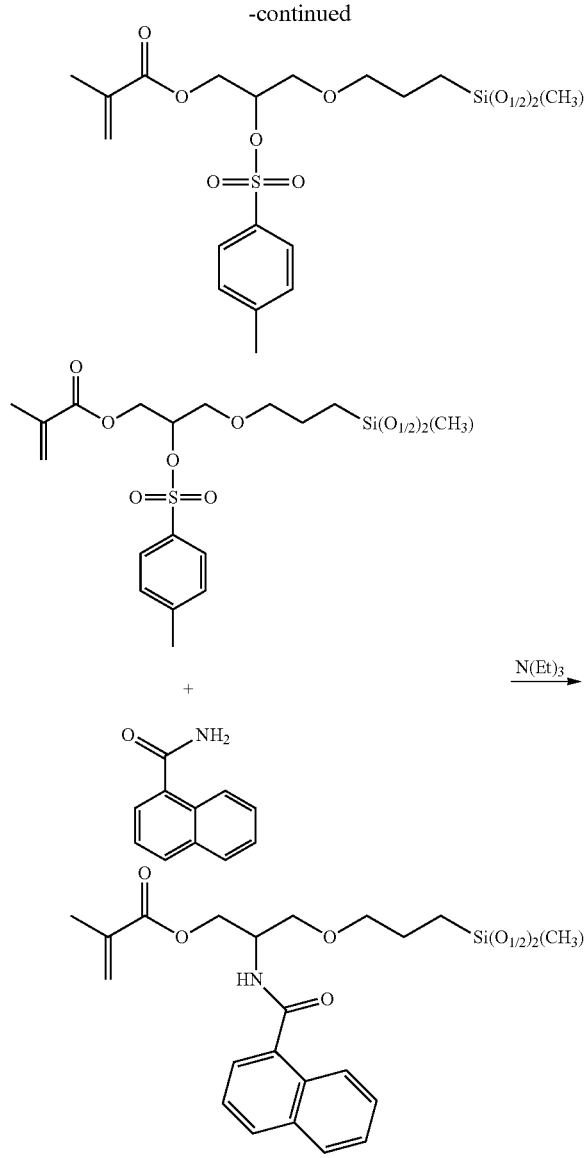

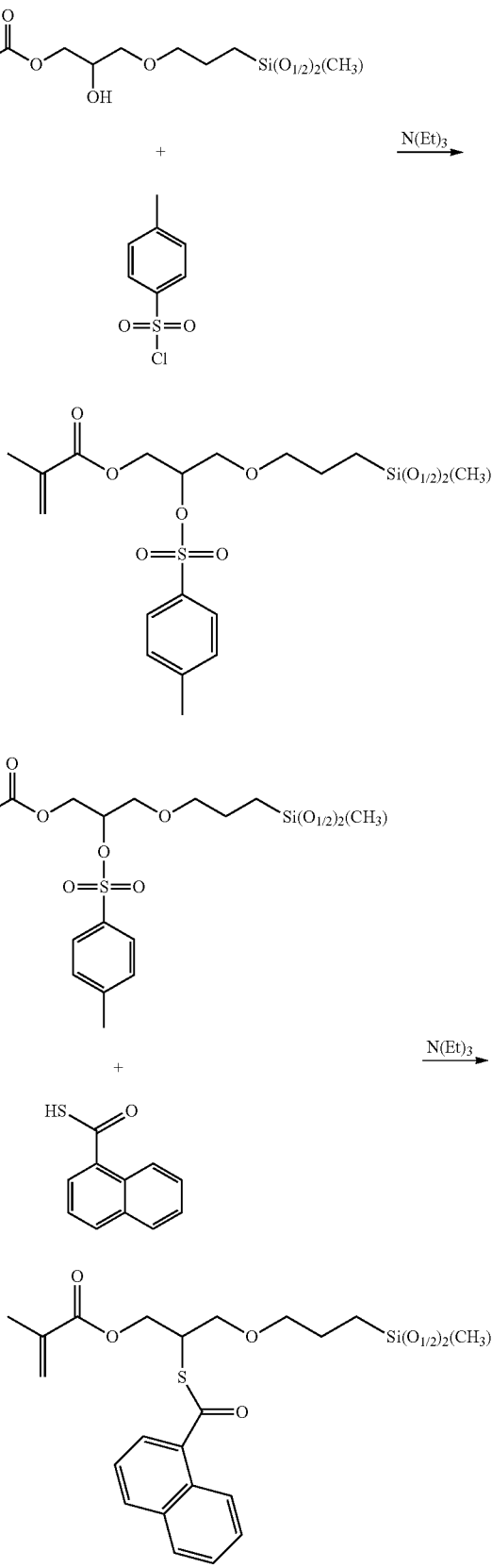

2.5) Preparation of a Polysiloxane Compound (Thioester) According to the Invention (Polysiloxane F) by Conversion of Polysiloxane a with (i) Para-Toluenesulfonyl Chloride and Subsequently with (ii) Naphthalene-1-Thiocarboxylic Acid (See Diagram (n)):

A solution of 16.5 mmol (1.1 eq.) para-toluenesulfonyl chloride in 50 ml of a mixture of acetone/toluene (volume ratio: 1:1) was mixed under ice cooling (4° C.) with 16.5 mmol triethylamine (1.1 eq.). The resulting mixture was subsequently mixed with 15 mmol polysiloxane A (1.0 eq.). Once mixing was complete the resulting clear solution was continually agitated at 4° C. for one hour. Afterwards, a solution of 1.1 eq. naphthalene-1-thiocarboxylic acid and 1.1 eq. triethylamine in 5 ml acetone/toluene (volume ratio: 1:1) was slowly added in drops. The resulting solution was heated to 75° C. and said temperature was maintained for 3 hours.

In a next step the solution was washed with water three times and the organic phase was dried over magnesium sulphate. Following removal of the solvent under vacuum a slightly yellowy flowable (liquid) resin with a viscosity of 15 Pa·s at 25° C., a refractive index no of 1.53, and a shrinkage of 3.6% was obtained. Table 2 provides a comparison of physical properties.

TABLE 2

Physical properties of polysiloxane compounds according to the invention (B, C, D, E, and F) compared with the polysiloxane A not according to the invention. *The "flexural strength" and "shrinkage" properties were determined in the cured state (see Points C-3 and C-4 below).

|  | Polysiloxane A (reference) | Polysiloxane B | Polysiloxane C | Polysiloxane D | Polysiloxane E | Polysiloxane F |
|---|---|---|---|---|---|---|
| Flexural strength* | 32 | 43 | 39 | 35 | 44 | 42 |
| Shrinkage* | 4.8 | 3.6 | 3.4 | 3.7 | 3.6 | 3.6 |
| Viscosity | 4.5 | 17.5 | 13.5 | 1.5 | 24 | 15 |
| Refractive index $n_D$ | 1.47 | 1.52 | 1.49 | 1.48 | 1.52 | 1.53 |

The viscosity of polysiloxanes according to the invention (polysiloxanes B, C, D, E, and F) is not disadvantageously changed compared with the viscosity of polysiloxanes not according to the invention (polysiloxane A) (in any event in the case of polysiloxanes B, C, E, and F the increase is insignificant).

Polysiloxane compounds according to the invention have a refractive index in the preferred area of 1.48 to 1.54 and thus a higher refractive index than the refractive index of 1.47 of the polysiloxane A not in accordance with the invention.

B) PREPARATION AND PROPERTIES OF CURABLE DENTAL MATERIALS (COMPOSITES A TO E)

In a 100 ml laboratory kneader the respective polysiloxane compounds (polysiloxane A, B, C, D, E, and F) and additional compounds/substances according to Table 3 were mixed together in the proportions indicated there, resulting in homogenous, paste-like formulations (precursors to a composite A not according to the invention and precursors to composites B to G according to the invention). Following de-aeration of the paste-like formulations under vacuum (at a pressure of 0.9 bar) the de-aerated, paste-like formulations (composites A to G) were characterised according to their flexural strength and their polymerisation shrinkages ("shrinkage"). A comparison of the results is shown in Table 4.

All details in Table 3 are given in weight percent, in relation to the total weight of the respective composite.

TABLE 3

Compositions of curable dental materials having as a basis polysiloxane compounds according to the invention (polysiloxanes B, C, D, E, and F (used in composites B to G)) or as a basis the polysiloxane A not according to the invention (used in composite A). All curable dental materials (composites) contain as initiators/inhibitors the same quantities of camphor quinone (0.4 wt. %) and dimethyl pare amino benzoic acid (0.6 wt. %) for initiation and the same quantities of butylhydroxytoluene (0.1 wt. %) for inhibition.

| Components | Composite A (reference) | Composite B | Composite C | Composite D | Composite E | Composite F | Composite G |
|---|---|---|---|---|---|---|---|
| Polysiloxane A | 20 | 0 | 0 | 0 | 0 | 0 | 0 |
| Polysiloxane B | 0 | 20 | 0 | 0 | 10 | 0 | 0 |
| Polysiloxane C | 0 | 0 | 20 | 0 | 0 | 0 | 0 |
| Polysiloxane D | 0 | 0 | 0 | 20 | 0 | 0 | 0 |
| Polysiloxane E | 0 | 0 | 0 | 0 | 0 | 20 | 0 |
| Polysiloxane F | 0 | 0 | 0 | 0 | 0 | 0 | 20 |
| BisGMA/TEGDMA in a mass ratio of 1:1 | 0 | 0 | 0 | 0 | 10 | 0 | 0 |
| Barium silicate glass (0.7 μm) silanised | 15.8 | 15.8 | 15.8 | 15.8 | 15.8 | 15.8 | 15.8 |
| Barium silicate glass (1.5 μm) silanised | 63.1 | 63.1 | 63.1 | 63.1 | 63.1 | 63.1 | 63.1 |
| Initiators/inhibitors | 1.1 | 1.1 | 1.1 | 1.1 | 1.1 | 1.1 | 1.1 |

TABLE 4

Physical properties and associated values of composites A, B, C, D, E, F, and G. The "flexural strength" and "shrinkage" properties were determined in the cured state (see Points C-3 and C-4 below).

| | Composite A | Composite B | Composite C | Composite D | Composite E | Composite F | Composite G |
|---|---|---|---|---|---|---|---|
| Flexural strength | 110 | 125 | 127 | 120 | 155 | 126 | 128 |
| Shrinkage | 1.5 | 1.2 | 1.1 | 1.3 | 1.9 | 1.2 | 1.2 |

The curable dental materials according to the invention (composites B to G) in the cured state have a higher flexural strength than the flexural strength of a curable dental material not according to the invention (composite A) comprising a polysiloxane A not according to the invention (as described above).

Curable dental materials according to the invention (composites B to D, and F and G) are also characterised in that they experience less shrinkage upon curing than a curable dental material not according to the invention (composite A) comprising a polysiloxane A not according to the invention (as described above).

C) METHODS OF DETERMINATION FOR DETERMINING THE PHYSICAL PROPERTIES OF THE POLYSILOXANE COMPOUNDS OR THE CURABLE DENTAL MATERIALS (COMPOSITES)

C-1) Determination of the Viscosity:

The viscosity was determined using a rheometer (Physica MCR 301) from Anton Paar. To do so in each case 4 g of the non-polymerised polysiloxane (polysiloxane A, B, C, D, E, or F) was evenly spread over a 50 mm rheometer plate. Then the material was sheared at 25° C. by means of a rotational movement (the shearing speed (shear rate) y was selected such that it covered a range of 0.5 to 10 $s^{-1}$). The viscosity of the material was determined at 20 measurement points which were in each case recorded at a 10 s interval. The last measurement point indicates the viscosity at maximum shear. The viscosity is shown in Table 2 above in Pa·s.

C-2) Determination of the Refractive Index:

The refractive index was determined by means of a refractometer (RE40) from Mettler Toledo in each case from 1 g of the non-polymerised polysiloxane (polysiloxane A, B, C, D, E, or F). The refractive index is a dimensionless physical variable.

C-3) Determination of the Flexural Strength:

The flexural strength of the polysiloxanes (polysiloxane A, B, C, D, E, or F, see Table 2, "flexural strength") or the curable dental materials (composites A to G, see Table 4, "flexural strength") was determined in accordance with FprEN ISO 4049 in each case from 5 correspondingly cured materials (test specimens) (see FprEN ISO 4049, points 7.11.3 and 7.11.4). The flexural strength is shown in the above Tables 2 and 4 in Megapascal (MPa).

For the investigations on the respective polysiloxanes A to F these were activated for curing by addition of in each case 3 g/kg camphor quinone and 4.5 g/kg dimethyl para amino benzoic acid. The activated polysiloxanes thus obtained were then in each case transferred into a Teflon mould (2 mm*2 mm*50 mm) and the top of the Teflon mould covered with an ethyl acetate film. The specimens obtained in this way were then exposed to light with a wavelength ranging from 400 to 500 nm in a light box for a period of 60 minutes, providing cured test specimens. These cured test specimens were then released from the Teflon mould and stored for 24 hours in a water bath with a water temperature of 37° C. The flexural strength was then measured using a force measuring device from Zwick Roell Z005 KAS-TC (year of construction 2007) at a force progression of 50±16 N/min.

The investigations on the respective composites (composites A to G, see the respective compositions according to Table 3) were performed under the same conditions and with the same methods (but without further addition of initiators such as camphor quinone and dimethyl para amino benzoic acid), as indicated above for the investigations on the polysiloxanes.

C-4) Determination of the Polymerisation Shrinkages:

The polymerisation shrinkages of the polysiloxanes (polysiloxane A, B, C, D, E, or F see Table 2, "Shrinkage") or of the curable dental material (see Table 4, "Shrinkage") were measured using the "Watts"* method on correspondingly cured dental materials. The polymerisation shrinkage ("Shrinkage") is shown in the above Tables 2 and 4 in percent by volume (vol. %), in relation to the volume of the test specimen prior to curing. The values shown in Tables 2 and 4 signify a volume reduction in percent following curing.

For the investigations on the respective polysiloxanes these were activated for curing with 3 g/kg camphor quinone and 4.5 g/kg dimethyl para amino benzoic acid. The shrinkage was investigated in the context of a photo-induced radical polymerisation with light of a wavelength ranging from 400 to 500 nm according to the "Watts" method.

The investigations on the respective composites (composites A to G, see the respective compositions according to Table 3) were performed similarly to the investigations on the polysiloxanes, but without further addition of initiators such as camphor quinone and dimethyl pare amino benzoic acid.

*Method according to Watts D. C., Cash A. J.: Determination of polymerization shrinkage kinetics in visible light cured materials: methods development, Dental Materials 1991; 7; 281

The invention claimed is:

1. A polysiloxane compound comprising:
   (A) one, two, three or more than three in each case structurally identical first siloxane units selected from the group consisting of siloxane units of the general formula (I)

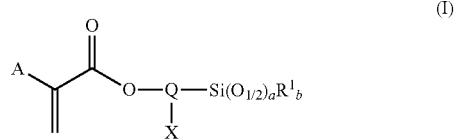

wherein for the structural units A, Q, X and $R^1$ in each of the structurally identical first siloxane units independently of one another the following applies:
A denotes H or $CH_3$,
Q denotes a link group bearing substituent X,
$R^1$ denotes an alkyl radical with a total of 1 to 4 carbon atoms and X is selected from the group consisting of
 branched, saturated, unsubstituted alkyl radical with a total of 7 to 18 carbon atoms,
 unbranched, saturated, unsubstituted alkyl radical with a total of 7 to 18 carbon atoms,
 unsubstituted or alkyl substituted aryl radical with a total of 10 to 18 carbon atoms, wherein the alkyl substituent in the alkyl substituted aryl radical is
 branched and saturated
 or
 unbranched and saturated
and
Z—(CO)—R², wherein herein for the structural units Z and R² independently of one another and independently of what the structural units A, Q and R¹ denote the following applies:
 Z denotes O, S or NH, preferably O
 and
 R² is selected from the group consisting of
  branched, saturated, unsubstituted alkyl radical with a total of 6 to 18 carbon atoms,
  unbranched, saturated, unsubstituted alkyl radical with a total of 6 to 18 carbon atoms, and
  unsubstituted or alkyl substituted aryl radical with a total of 9 to 18 carbon atoms, wherein the alkyl substituent in the alkyl substituted aryl radical is
  branched and saturated
  or
  unbranched and saturated,
 wherein
 b denotes 0, 1 or 2 and
 a denotes 3-b.

2. The polysiloxane compound, according to claim 1, comprising:
(A) one, two, three or more than three in each case structurally identical first siloxane units selected from the group consisting of siloxane units of the general formula (Ia)

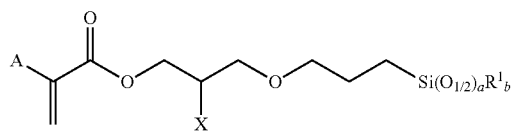

wherein for the structural units A, X and R¹ in each of the structurally identical first siloxane units independently of one another the following applies:
A denotes H or CH₃,
R¹ denotes an alkyl radical with a total of 1 to 4 carbon atoms
and
X is selected from the group consisting of
 branched, saturated, unsubstituted alkyl radical with a total of 7 to 18 carbon atoms,
 unbranched, saturated, unsubstituted alkyl radical with a total of 7 to 18 carbon atoms,
 unsubstituted or alkyl substituted aryl radical with a total of 10 to 18 carbon atoms, wherein the alkyl substituent in the alkyl substituted aryl radical is
 branched and saturated
 or
 unbranched and saturated
and
Z—(CO)—R², wherein herein for the structural units Z and R² independently of one another and independently of the meaning of the structural units A and R¹ the following applies:
 Z denotes O, S or NH,
 and
 R² is selected from the group consisting of
  branched, saturated, unsubstituted alkyl radical with a total of 6 to 18 carbon atoms,
  unbranched, saturated, unsubstituted alkyl radical with a total of 6 to 18 carbon atoms, and
  unsubstituted or alkyl substituted aryl radical with a total of 9 to 18 carbon atoms, wherein the alkyl substituent in the alkyl substituted aryl radical is
  branched and saturated
  or
  unbranched and saturated,
 wherein
 b denotes 0, 1 or 2 and
 a denotes 3-b
and
(B) one, two, three or more than three, in each case structurally identical second siloxane units, which are structurally different from the first siloxane unit.

3. The polysiloxane compound according to claim 1, comprising:
(A) one, two, three or more than three in each case structurally identical first siloxane units selected from the group consisting of siloxane units of the general formula (Ic)

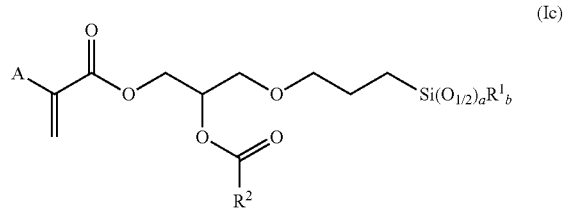

wherein for the structural units A, R¹ and R² in each of the structurally identical first siloxane units independently of one another the following applies:
A denotes H or CH₃,
R¹ denotes an alkyl radical with a total of 1 to 4 carbon atoms,
and
R² is selected from the group consisting of
 branched, saturated, unsubstituted alkyl radical with a total of 6 to 18 carbon atoms,
 unbranched, saturated, unsubstituted alkyl radical with a total of 6 to 18 carbon atoms, and
 unsubstituted or alkyl substituted aryl radical with a total of 9 to 18 carbon atoms, wherein the alkyl substituent in the alkyl-substituted aryl radical is
 branched and saturated
 or
 unbranched and saturated,
wherein
 b denotes 0, 1 or 2 and
 a denotes 3-b
and
(B) one, two, three or more than three, in each case structurally identical second siloxane units, which are structurally different from the first siloxane unit.

4. The polysiloxane compound according claim 1, wherein $R^2$ is selected from the group consisting of:
1-naphthyl,
4-tert.-butyl-1-phenyl,
and
n-undecanyl.

5. A curable dental material comprising:
one or more than one polysiloxane compound according to claim 1,
and
one or more than one compound different from the polysiloxane compound according to claim 1.

6. The curable dental material according to claim 5, further comprising one, two or more than two or all substances from the group consisting of:
dental organic filler particles, which are radiopaque and/or nanoscale,
dental inorganic filler particles which are radiopaque and/or nanoscale,
dental organically surface-modified inorganic filler particles, which are radiopaque and/or nanoscale,
rheological agents,
polymerisation initiators, photoinitiators,
chemical compounds as catalysts or components of catalyst systems,
colourants, dye pigments,
stabilisers, daylight stabilisers,
inhibitors,
activators,
molecular weight modifiers,
preservatives,
surface-active substances,
microbicides, bactericides,
organic radically polymerisable monomers, which are not polysiloxanes according to the invention, for conversion with the polysiloxane compound according to the invention,
organic polymers and oligomers and compounds with high molecular weights, plasticisers,
thickeners and
dental medicinal products.

7. The cured dental material, obtainable from a curable dental material according to claim 5 by means of polymerisation of the polysiloxane compound contained in the dental material and possibly further polymerisable components contained in the dental material.

8. The polysiloxane compound according to claim 1, for application in a therapeutic procedure, wherein a polysiloxane compound according to claim 1 is used as a polymerisable component of a curable dental material.

9. The polysiloxane compound according to claim 1, for specific application in a therapeutic procedure for temporary or permanent filling of a dental cavity
or
in a therapeutic procedure as a
dental filling material,
dental lining material,
dental adhesive (bonding),
as a flowable composite material (flow material),
as a fissure sealant,
as a crown material,
as an inlay and/or onlay,
as a bridge material
and/or as a core build-up material.

10. A kit, comprising:
one, two or more than two curable dental materials according to claim 5
and/or
one, two or more than two base pastes and one, two or more than two catalyst pastes, wherein the one base paste or the two or more than two base pastes in each case and independently of one another comprises or comprise one or more than one polysiloxane compound according to claim 1.

11. A method for preparing a polysiloxane compound, comprising the following steps:
preparing or providing an intermediate polysiloxane compound comprising
($A_p$) one, two, three or more than three in each case structurally identical first intermediate siloxane units selected from the group consisting of siloxane units of the general formula ($I_p$)

$$A\underset{\underset{\displaystyle X_P}{|}}{\overset{\overset{\displaystyle O}{\|}}{C}}-O-Q-Si(O_{1/2})_a R^1_b \quad (I_P)$$

wherein for the structural units A, Q, $X_p$ and $R^1$ in each of the structurally identical first siloxane units independently of one another the following applies:
A denotes H or $CH_3$,
Q denotes a link group bearing the substituent $X_p$,
$R_1$ denotes an alkyl radical with a total of 1 to 4 carbon atoms
and
$X_p$ for a reactive group
wherein
b denotes 0, 1 or 2 and
a denotes 3-b,
conversion of the intermediate polysiloxane compound in one or more steps through reaction of the reactive group $X_p$, so that the polysiloxane compound according to claim 1 is formed.

12. The method for preparing a curable dental material comprising the steps of:
providing or preparing one or more polysfoxane compounds according to claim 1,
providing or preparing one, more additives,
preparing a single-component or multi-component system comprising the provided or prepared polysiloxane compound(s) and the provided or prepared substance(s) and optionally, additional substances,
wherein multi-component systems substances that trigger a polymerisation are distributed over separate components such that a polymerisation of the polysiloxane compounds is triggered through mixing of said components.

13. A method for preparing a cured dental material comprising the following steps:
providing or preparing a curable dental material according to claim 5,
polymerisation of the polysiloxane compound contained in the dental material and possibly further polymerisable components contained in the dental material.

14. A method comprising of:
Application of a curable dental material according to claim 5
on the tooth substance or the dental tissue of a patient
or
on a dental restoration.

* * * * *